(12) United States Patent
Shimizu et al.

(10) Patent No.: US 6,548,272 B1
(45) Date of Patent: Apr. 15, 2003

(54) GENE ENCODING FOR A TRANSMEMBRANE PROTEIN

(75) Inventors: Nobuyoshi Shimizu, Chiba (JP); Kentaro Nagamine, Tochigi (JP)

(73) Assignee: Eiken Kagaku Kabushiki Kaisya, Tokyo (JP)

( * ) Notice: Subject to any disclaimer, the term of this patent is extended or adjusted under 35 U.S.C. 154(b) by 0 days.

(21) Appl. No.: 09/600,087

(22) PCT Filed: Nov. 11, 1999

(86) PCT No.: PCT/JP99/06289
§ 371 (c)(1),
(2), (4) Date: Jul. 11, 2000

(87) PCT Pub. No.: WO00/29571
PCT Pub. Date: May 25, 2000

(30) Foreign Application Priority Data

Nov. 12, 1998 (JP) ............................................. 10-321200

(51) Int. Cl.[7] ........................... C12N 15/12; C12N 5/10; C12N 15/63; C07K 14/705
(52) U.S. Cl. ...................... 435/69.1; 530/350; 435/71.1; 435/71.2; 435/252.3; 435/254.11; 435/471; 435/325; 435/320.1
(58) Field of Search ............................... 536/23.1, 23.5; 530/350; 435/69.1, 71.1, 71.2, 471, 252.3, 254.11, 325, 320.1

(56) References Cited

PUBLICATIONS

Mikayama Et Al. Proc. Natl. Acad. Sci. USA vol. 90, pp. 10056–10060, 1993.*
Voet Et Al. Biochemistry, John Wiley & Sons, Inc. pp. 126–128 & 228–234, 1990.*

Miron Baron et al., A Possible Vulnerability Locus for Bipolar Affective Disorder on Chromosome 21q22.3, Nature Genetics, vol. 8, pp. 291–296 (1994).

T. Furusho et al., Clinical DNA Diagnosis Method (in Japanese), Kanehara Shuppan K.K., pp. 170–177 (1995).

Jun Kudoh et al., Localization of 16 Exons to a 450–kb Region Involved in the Autoimmune Polyglandular Disease Type I, (APECED) on Human Chromosome 21q22.3, DNA Research, vol. 4, pp. 45–52 (1997).

Nobuyoshi Shimizu et al., Molecular Cloning of a Novel Putative Ca2+ Channel Protein (TRPC7) Highly Expressed in Brain, Genomics, vol. 54, pp. 124–131 (1998).

A. Elson et al., The Structure of the Human Liver–Type Phosphofructokinase Gene, Genomics, vol. 7, pp. 47–56 (1990).

N. Shimizu et al., Transcriptional Mapping and Genomic Sequencing of the Down Syndrome Critical Region of Human Chromosome 21, Cytogenet Cell Genet, vol. 79, pp. 44–45 (1997).

* cited by examiner

*Primary Examiner*—Prema Mertz
(74) *Attorney, Agent, or Firm*—Fish & Richardson PC

(57) ABSTRACT

A gene for a novel transmembrane protein was isolated and its nucleotide sequence was determined. A protein encoded by this gene (TRPC7) has 7 transmembrane regions, and because there is homology with TRP (transient receptor potential), this protein is considered to have calcium channel functions. Further, since a mutation in the TRPC7 gene is frequently observed in patients with manic-depressives insanity, TRPC7 is considered to be a pathogenic gene for bipolar affective disorder.

11 Claims, 4 Drawing Sheets

```
               2                          .*.    3*  .  *  .  *.
TRPC7   -SVDNGLWRVTLCMLAFPLLLTGLISFREKRLQDVGTPAARARAFFTAPVVVFHLNILSY    806
Htrp-3  YENLSGLREQTIAIKCLVVLVVALG-LPFLAIGYWIAPCSRLGKILRSPFMKFVAHAASF    393
Htrp-1  -GQMSGYRRKPTCKKIMTVLTVGIF-WPVLSLCYLIAPKSQFGRIIHTPFMKFIIHGASY    394
D.trp   ---------------LMDVVKLGCS-FPIYSLKYILAPDSEGAKFMRKPFVKFITHSCSY    377
D.trpl  ---------------VICIAQVAVL-FPLYCLIYMCAPNCRTGQLMRKPFMKFLIHASSY    384
                                    S1                            S2

**                             .         .       .
TRPC7   FAFLCLFAYVLMVDFQP----------------------VPSWCECAIYLWLFSLVCE    842
Htrp-3  IIFLGLLVFNASDRFEGITTLPNIT--VTDYPKQIFRVKTTQFTWTEMLIMVWVLGMMWS   451
Htrp-1  FTFLLLLNLYSLVYNED----------------KKNTMGPALERIDYLLILWIIGMIWS   437
D.trp   MFFLMLLGAASLRVVQITFELLAFPWMLTMLEDWRKHERGSLPGPIELAIITYIMALIFE   437
D.trpl  LFFLFILILVSQRADDDFVRIFGTTRMKKELAEQELRQRGQTPSKLELIVVMYVIGFVWE   444

. . .       *       .     4 *     . . .
TRPC7   EMRQLFYDPDECGLMKKAALYFSDFWNKLDVGAILLFVAGLTCR---LIPAT--------   891
Htrp-3  ECKELWLE----GPRE----YILQLWNVLDFGMLSIFIAAFTARFLAFLQATKAQQYVDS   503
Htrp-1  DIKRLWYE----GLED----FLEESRNQLSFVMNSLYLATFALKVVAHNKFH--------   481
D.trp   ELKSLYSD----GLFE----YIMDLWNIVDYISNMFYVTWILCRATAWVIVHR-------   482
D.trpl  EVQEIFAV----GMKS----YLRNMWNFIDFLRNSLYVSVMCLRAFAYIQQAT-------   489
                                        S3
                            *     5.      . .     .
TRPC7   ------------------------LYP--G-RVILSLDFILFCLRLMHIFTISKTL   920
Htrp-3  YVQESDLSEVTLPPEIQYFTYARDKWLPSDPQIISEGLYAIAVVLSFSRIAYILPANESF   563
Htrp-1  --------DFAD----------RKDWDAFHPTLVAEGLFAFANVLSYLRLFFMYTTSSIL   523
D.trp   --------DLWFRGIDPYF--PREHWHPFDPMLLSEGAFAAGMVFSYLKLVHIFSINPHL   532
D.trpl  --------EIARDPQMAYI--PREKWHDFDPQLIAEGLFAAANVFSALKLVHLFSINPHL   539
                                                    S4

**   . . .  6*  *     .     *     .
TRPC7   GPKIIIVKRMMKDVFFFLFLLAVWVVSFGVAKQAILIHNERRVDWLFRGAVYHSYLTIFG   980
Htrp-3  GPLQISLGRTVKDIFKFMVLFIMVFFAFMIGMFILYSY--YLGAKVN-------------   608
Htrp-1  GPLQISMGQMLQDFGKFLGMFLLVFSFTIGLTQLYDKG-YTSKEQKDCVGIFCEQQSND   582
D.trp   GPLQVSLGRMIIDIIKFFFIYTLVFAFGCGLNQLLWY--YAELEKNKCYHLHPDVADFD   590
D.trpl  GPLQISLGRMVIDIVKFFFIYTLVFAFACGLNQLLWY--FAALEKSKCYVLPGGEADWG   597
                    S5

7    . * .
TRPC7   QIPG----YIDGVNFNPEHCSPNGTDPYKPKCPESD-ATQQRPAFPEWLTVLLLCLYLLF   1035
Htrp-3  ---------AAFTTVEESFKTLFWSIFGLSEVTSVV--LKYDHKFIENIGYVLYGIYNVT   657
Htrp-1  ---------TFHSFIGTCFALFWYIFSLAHVAIFVTRFSYGEELQSFVGAVIVGTYNVV   632
D.trp   DQEKACTIWRRFSNLFETSQSLFWASFGLVDLVSFD--LAGIKSFTRFWALLMFGSYSVI   648
D.trpl  SHGDSCMKWRRFGNLFESSQSLFWASFGMVGLDDFE--LSGIKSYTRFWGLLMFGSYSVI   655
                                                         S6

*  .***   ..    .       *  *** *   *  *'     .  ****  .
TRPC7   TNILLLNLLIAMFNYTFQQVQEHTDQIWKFQRHDLIEEYHG-RPAAPPPFILLSHLQ   1091
Htrp-3  MVVVLLNMLIAMINSSYQEIEDDSDVEWKFARSKLWLSYFDDGKTLPPPFSLVPSPK   714
Htrp-1  VVIVLTKLLVAMLHKSFQLIANHEDKEWKFARAKLWLSYFDDKCTLPPPFNIIPSPK   689
D.trp   NIIVLLNMLIAMMSNSYQIISERADTEWKFARSQLWMSYFEDGGTIPPPFNLCPNMK   705
D.trpl  NVIVLLNLLIAMMSNSYAMIDEHSDTEWKFARTKLWMSYFEDSATLPPPFNVLPSVK   712
```

GENE ENCODING FOR A TRANSMEMBRANE PROTEIN

FIELD OF THE INVENTION

The present invention relates to a human novel gene and in particular to a gene for a novel transmembrane protein considered to be a pathogenic gene for bipolar affective disorder.

BACKGROUND ART

Bipolar affective disorder is a disease occurring mainly at an age of about twenty years old, to the middle age and constitutes one of two major endogenous psychoses along with schizophrenia. The center of its mental symptoms is emotional impairment, and this disease is characterized that even after the morbid phase occurs repeatedly during a periodic course, the patient is restored to normal mental conditions without having mental ruin (impaired conditions). The morbid phase includes a manic state showing high emotion and promoted willingness and a depressive state of emotion, and each morbid phase (for a few weeks to a few months) repeatedly appears or both the morbid phases appear alternately, but in some cases the morbid phase may end only once. For treatment of this disease, an antidepressant or an anti-psychosis medicine is used, and by the advent of lithium salts, chemotherapy has occupied the most important position.

The morbidity risk factor of this disease is estimated to be approximately 0.4% of the population, but in consideration in mild cases not necessitating medical treatment, the morbidity may considerably exceed this figure. The morbidity according to a fact-finding survey conducted in 1963 by the Ministry of Health and Welfare was 0.02%, but naturally this morbidity does not cover non-manifested cases at the time of the survey. In the incidence of this disease, there is a certain difference depending on human race, differentiation and region, and it is noted that the incidence tends to be high in highly differentiated races or in upper classes. It is said that the number of female patients is higher than male patients, but this is necessarily not evident in Japan.

This disease is classified into a unipolar type (type showing the depressive phase only) and a bipolar type (type showing both the phases or the manic phase only), and comparison between the unipolar type and the bipolar type indicates that the incidence of the unipolar type is considerably higher at a ratio of 1:6 to 10. In particular, this trend is significant at the middle age or thereafter.

Diagnosis of bipolar affective disorder is made according to clinical symptoms based on emotional impairment. There is also a report that the level of serotonin or noradrenaline is varied with emotional impairment, and particular attention is paid to the movement of monoamine metabolism-related substances in blood, urine, or cerebrospinal fluid. Further, attention is also paid to impairments in the endocrine functions of the thyroid gland, adrenal cortex etc. and abnormalities in the metabolism of electrolytes affecting the mechanism of neurotransmission, but there is no established method for clinical examination utilizable for diagnosis thereof.

It is considered that a genetic predisposition plays an important role in the onset of bipolar affective disorder. According to a lineage study (empirical hereditary prognosis), the morbidity risk factor of a patient's family is significantly higher than ordinary persons. The morbidity in such a family is estimated to be nearly 10 to 15% and there is no significant difference among patient's brothers, parents and children. According to a recent study, however, bipolar affective disorder is genetically not necessarily a single unit, and the morbidity risk factor of bipolar bipolar affective disorder in the family is genetically higher than that of unipolar depressive insanity in the family, and it is pointed out that generally, in a family of a patient with the bipolar type, the percentage of patients with the bipolar type in the family is relatively high, while in a family of a patient with the unipolar type, the percentage of patients with the unipolar type in the family is relatively high.

In study by a twins method, the involvement of a genetic predisposition is evident, and the morbidity of the disease in both one-egg twins is significantly higher than in both two-egg twins. However, because there is not few exceptional cases, it is considered that the expression of a gene for bipolar affective disorder is considerably affected by the environment as is the case with a gene for schizophrenia [1].

The hereditary mode of bipolar affective disorder, excluding a limited number of families having considerably negative factors in the family, cannot be elucidated in terms of the Mendelian heredity concerned with a single gene, so it is considered that the majority of cases are due to polyfactor-polygene heredity in which a plurality of genes and environmental factors are involved. Further, endogenous factors in bipolar affective disorder, that is, disease-specific changes in organs, biological markers, onset mechanism etc. are not revealed, thus making genetic study further difficult.

In 1987, Egeland et al. reported that there is a strong linkage between chromosome 11q15 HRAS1 and INS genes and bipolar affective disorder [2]. At the same time, in a study where color blindness in the chromosome Xq28 and GP6D were used as markers in a family liable to bipolar impairment, Baron et al. reported that there is a strong linkage thereof to bipolar impairment [3]. However, these and later reports showed some results denying the linkage, and the above study is not an established finding. Besides, regions having a high linkage to bipolar affective disorder include Xq29-27 [4], 4q16 [5], 18q22-23 [6], 18centro [7] and 21q22.3 [8].

However, in the linkage study of bipolar affective disorder, a large number of findings suggesting the linkage are obtained while there are many results denying these findings [9] so that a state of confusion continues. As a result, none of these findings are established, and at present, there is no cloned gene for bipolar affective disorder [10].

DISCLOSURE OF INVENTION

The problem to be solved by the invention is to determine the nucleotide sequence of a pathogenic gene for bipolar affective disorder as well as the amino acid sequence of a protein encoded by said nucleotide sequence.

As a result of their eager study for solving the problem described above, the present inventors isolated a new gene from human chromosome 21q22.3 region and determined its nucleotide sequence. Genes from patients with bipolar affective disorder were amplified by PCR using primers set up on the basis of said nucleotide sequence and analyzed, and as a result it was confirmed that there was a deletion in exon 5 in 10 samples out of 20 samples from patients with bipolar bipolar affective disorder. Accordingly, it is considered that this gene is a pathogenic gene for bipolar affective disorder.

It was revealed that the open reading frame of this gene designated TRPC7 codes for a protein with a molecular weight of 171,217 consisting of 1,503 residues having 7 transmembrane regions. Further, as a result of a search for homology in a database, said protein showed homology with Drosophila TRP (transient receptor potential) protein and human TRP protein as calcium channels.

An object of the present invention is to provide a polypeptide particularly a polypeptide shown in SEQ ID NO:2, which was designated TRPC7 because of its homology with known amino acid sequences such as Drosophila TRP protein and human TRP protein. TRPC7 has seven transmembrane regions similar to other TRPs and is estimated to act as a calcium channel.

A further object of the present invention is to provide a polynucleotide coding for TRPC7, in particular a polynucleotide coding for the polypeptide designated TRPC7 in the present specification. A particularly preferable example of this mode of the present invention is a polynucleotide comprising a region coding for human TRPC7 in the sequence shown in SEQ ID NO:1.

According to this mode of this invention, there are provided isolated nucleic acid molecules coding for human TRPC7, including mRNA, cDNA, genomic DNA and fragments thereof, and in a further specific example of this mode, there are provided biologically, diagnostically, clinically or therapeutically useful fragments thereof, including varieties, analogues or derivatives thereof or fragments of the varieties, analogues or derivatives. A particularly preferable example of this mode of this invention is varieties of a natural allele of human TRPC7.

An object of this invention is to provide a TRPC7 polypeptide in particular a human TRPC7 polypeptide which can be used in treatment of bipolar affective disorder. According to this mode of this invention, there is provided a novel human-derived polypeptide designated TRPC7 in this specification, as well as biologically, diagnostically or therapeutically useful fragments, varieties and derivatives thereof, varieties and derivatives of these fragments, and analogues thereof. A particularly preferable example of this mode according to this invention is varieties of human TRPC7 encoded by a natural allele of human TRPC7 gene. According to another mode of this invention, there is provided a method of screening a compound binding to the polypeptide of the present invention to activate or inhibit it.

A further object of this invention is to provide a method of producing said polypeptide, polypeptide fragments, varieties and derivatives, fragments of the varieties and derivatives, and analogues thereof. According to a preferable example of this mode, there is provided a method of producing said TRPC7 polypeptide, wherein host cells containing a human TRPC7-coding nucleotide sequence integrated therein and induced extraneously to be expressible are cultured under conditions for expression of human TRPC7 in the host and the polypeptide thus expressed is recovered.

According to a further other object of this invention, there are provided a product, a composition, a process and a method for utilizing said polypeptide and polynucleotide in particular for research, biological, clinical and therapeutic purposes.

According to a preferable example of this mode of the present invention, there are particularly provided a product, a composition and a method for the following purposes: evaluation of TRPC7 expression in cells by measuring the TRPC7 polypeptide or TRPC7 mRNA; treatment in vitro, ex vivo or in vivo of bipolar affective disorder by exposing cells to the TRPC7 polypeptide or polynucleotide disclosed in this specification; analysis of genetic deformation and defects such as deletions in TRPC7 gene; and increase of TRPC7 function or improvement of TRPC7 malfunction by administering the TRPC7 polypeptide or polynucleotide to creatures. According to a other embodiment of this invention, there is provided a method of using an active compound for stimulating the receptor polypeptide of this invention, to treat symptoms related to deficient expression of TRPC7. According to a still other embodiment of this invention, there is provided a method of using an inhibitory compound for treatment of symptoms accompanying excessive expression of TRPC7.

According to a further other mode of this invention, there are provided synthetic or recombinant TRPC7 polypeptide, conservatively substituted polypeptides thereof and derivatives thereof, an antibody and an anti-idiotype antibody against the same, which are used in diagnosis, therapy and/or research.

A further other object of this invention is to provide synthetic, isolated or recombinant polypeptides designed as subtype to inhibit or mimic TRPC7 or various fragments thereof. According to these examples or other examples of a further other mode of this invention, a probe hybridizing with the human TRPC7 sequence is provided. In a further preferable mode of this invention, an antibody against TRPC7 polypeptide is provided. In a very preferable example in this respect, the antibody is very selective against human TRPC7. According to another mode of this invention, TRPC7 agonist is provided. A preferable agonist is a molecule mimicking TRPC7, a TRPC7-binding molecule, or a molecule inducing or increasing TRPC7-inducing response. Further, a preferable agonist is a molecule which interacts with TRPC7, TRPC7 polypeptides or other modulators for TRPC7 activity thereby activating or increasing one or more effects of TRPC7. According to another mode of this invention, TRPC7 antagonist is provided. A preferable antagonist mimics TRPC7, thus binding to a TRPC7-binding molecule, but does not induce one or more responses for inducing TRPC7. Further, a preferable antagonist is a molecule binding to TRPC7 or interacting with it to inhibit one or more effects of TRPC7 or to prevent expression of TRPC7. According to an additional mode of this invention, there is provided a TRPC7 polynucleotide or a composition comprising the TRPC7 polynucleotide, which is administered into cells in vitro, ex vivo and in vivo or into multicellular creatures. In a particular preferable example in this mode of the present invention, said composition comprises the TRPC7 polynucleotide for expressing TRPC7 polypeptide in a host for treatment of the disease. Its expression in a patient with bipolar affective disorder is particularly preferable in this respect.

Other objects, features, advantages and modes of the present invention will be obvious to those skilled in the art in view of the following description of this specification. However, the description and the examples below are preferable modes of this invention and are shown merely for illustrative purposes. From the following description and other disclosure of this specification, it would be evident to those skilled in the art that various alternations and modifications are possible within the scope described in this specification. The drawings also show merely illustrative examples of this invention, and are not intended to limit the disclosure of the invention disclosed in this specification.

BRIEF DESCRIPTION OF THE DRAWINGS

FIG. 3 shows comparison among amino acid sequences of transmembrane regions in various TRP proteins.

BEST MODE FOR CARRYING OUT THE INVENTION

Figure 1:
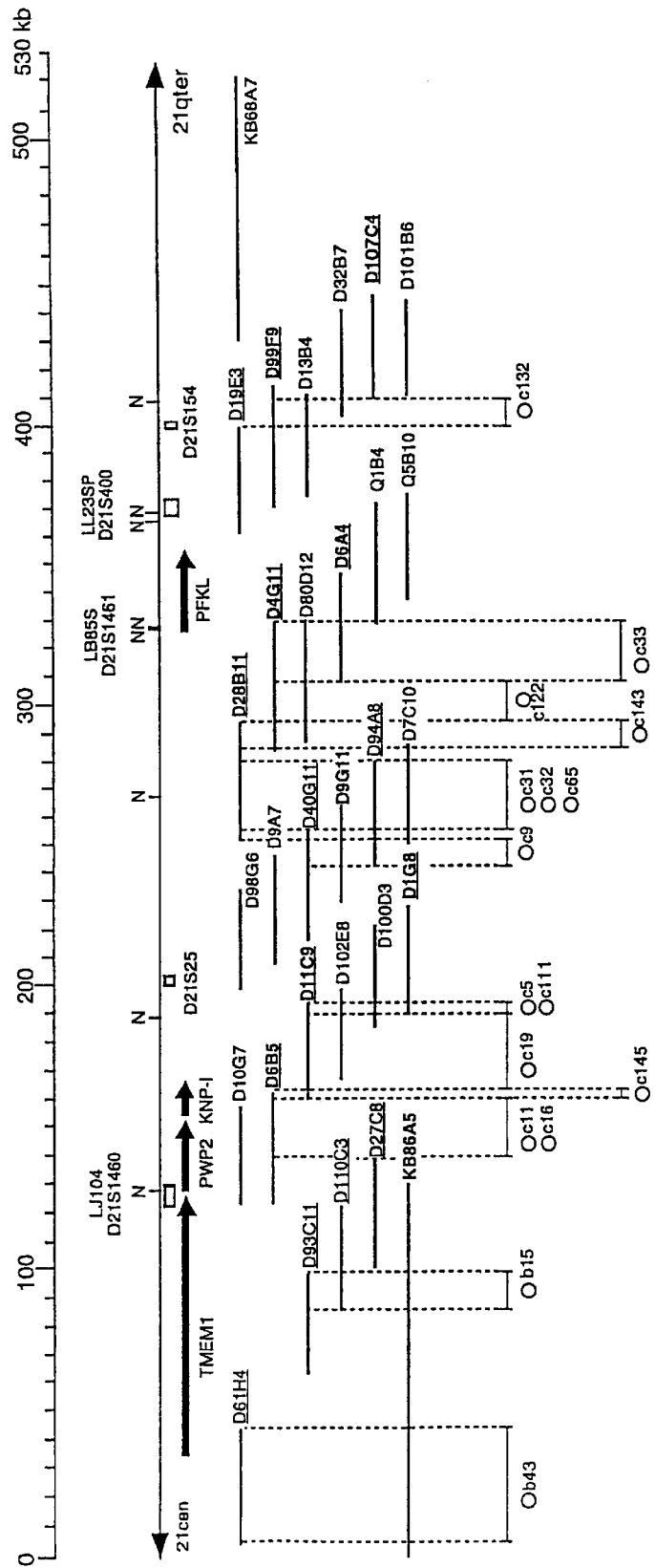
FIG. 1 shows a cosmid contig constructed from human chromosome 21q22.3 region.

The polynucleotide of the present invention may be in the form of RNA such as mRNA, or DNA encompassing cDNA and genomic DNA obtained by e.g. cloning techniques, chemical synthetic techniques or a combination thereof. The DNA may be an either double- or single-stranded chain. The single-stranded DNA may be a coding chain also known as a sense chain or a non-coding chain also known as an antisense chain. The coding chain coding for the polynucleotide may be identical to a coding sequence in the polynucleotide shown in SEQ ID NO:1. Further, as a result of overlapping (degeneracy) of genetic code, it may be a polynucleotide having a different sequence from a sequence coding for the polypeptide in SEQ ID NO:2.

The polynucleotide of this invention coding for the polypeptide in SEQ ID NO:2 includes, but is not limited to: a coding region for the mature polypeptide; a coding sequence for the mature polypeptide such as pre-, pro- or prepro-protein sequence plus an additional coding sequence such as a sequence coding for a leader or a secretory sequence; a coding sequence for the mature polypeptide with or without said additional sequence, plus an additional non-coding sequence including non-coding 5' and 3' sequences and introns such as a non-translating sequence transcribed, which play a role in mRNA processing for stability and in ribosome binding of mRNA including transcription, splicing and polyadenylation signal. A further functional coding region may also be integrated in said polypeptide. That is, the polypeptide may be fused to e.g. a marker sequence such as peptide to facilitate purification of the resulting fusion polypeptide. In a certain preferable example in this mode of this invention, the marker sequence is a hexahistidine peptide such as a HA tag attached to a pQE vector (Qiagen, Inc.). For example, hexahistidine provides convenient purification for a fusion protein [11]. The HA tag is an epitope derived from an influenza erythrocyte-coagulating protein [12], and a large number of other tags are also commercially available.

According to the foregoing description, the phrase "polynucleotide coding for the polypeptide" includes, due to degeneracy of genetic code, a polynucleotide containing any sequences coding for the polypeptide of this invention, particularly for human TRPC7 having the amino acid sequence shown in SEQ ID NO:2. This phrase also encompasses a polynucleotide containing a single continuous region or non-continuous regions (interrupted by e.g. an intron) and an additional region which may contain a coding and/or non-coding region. Further, the present invention relates to varieties of the above-described polynucleotide coding for fragments, analogues and derivatives of a polypeptide having the estimated amino acid sequence shown in SEQ ID NO:2. The varieties of said polynucleotide may be natural varieties such as natural allele varieties or varieties not known in the nature. Such non-natural polynucleotide varieties can be created by mutagenic techniques including those applied to polynucleotides, cells or creatures.

In this respect, there are varieties which are differentiated from said polynucleotide by the replacement, deletion or addition of a base. This includes the replacement, deletion or addition of one or more bases. The varieties may be altered in the coding region and/or non-coding regions. This alteration in the coding region can generate the replacement, deletion or addition of conserved or non-conserved amino acids. In this respect, a particularly preferable embodiment of this invention is a polynucleotide coding for a polypeptide having the amino acid sequence of TRPC7 shown in SEQ ID NO:2 and varieties, analogues, derivatives and fragments thereof, as well as fragments of said varieties, analogues and derivatives. Those particularly preferable in this respect are polynucleotides coding for varieties, analogues, derivatives and fragments of TRPC7 wherein in the amino acid sequence of the TRPC7 polypeptide shown in SEQ ID NO:2, a few amino acid residues or 5 to 10, 1 to 5, 1 to 3, 2, 1 or 0 amino acid residue has been replaced, deleted and/or added, as well as varieties, analogues and derivatives of said fragments. Among these, silent replacement, addition and deletion not changing the properties and activity of TRPC7 are particularly preferable. Conservative replacement is also particularly preferable in this respect. The most preferable one is a polynucleotide coding for a polypeptide having the unsubstituted amino acid sequence of SEQ ID NO:2.

A more preferable example of this invention is a polynucleotide having at least about 70% homology with a polynucleotide coding for the TRPC7 polypeptide having the amino acid sequence shown in SEQ ID NO:2, as well as a polynucleotide complementary to such a polynucleotide. In this respect, a polypeptide with at least 90% homology with said polynucleotide is very preferable, and a polypeptide with at least 95% homology therewith is especially preferable. Further, the polynucleotide has preferably at least 97%, more preferably at least 95 to 99%, most preferably at least 99% homology therewith. Further, a particularly preferable example in this respect is the mature polypeptide encoded by cDNA in SEQ ID NO:2 and a polynucleotide coding for a polypeptide having substantially the same biological function or activity as that of the mature polypeptide.

Further, the present invention relates to a polynucleotide hybridizing with said sequence. In this respect, the present invention relates to a polynucleotide hybridizing with said polynucleotide under stringent conditions. The "stringent conditions" used in this specification means that hybridization occurs between two sequences only when there is at least 95% homology, preferably at least 97% homology therebetween. As will be further examined for analysis of the polynucleotide of this invention, the polynucleotide of this invention described above can be used e.g. as a hybridization probe for cDNA and genomic DNA for isolation of full-length cDNA and genomic clones coding for TRPC7 and further for isolation of other gene cDNA and genomic clones having high sequence analogy to human TRPC7 gene. Such probe consists generally of at least 15 bases. Preferably, such a probe possesses at least 30 bases and may possess at least 50 bases. A particularly preferable probe is in the range of 30 to 50 bases.

For example, the coding region for the TRPC7 gene can be isolated by screening with an oligonucleotide probe using a known sequence. Then, a labeled oligonucleotide complementary to the sequence of the gene of this invention is used for screening of human cDNA, genomic DNA or mRNA library to determine a polynucleotide hybridized by the probe. As examined for the polynucleotide in this specification, the polynucleotide and polypeptide according to the present invention can be used as study reagents and materials for therapy and diagnosis of the human disease.

The polynucleotide may code for a polypeptide having additional N- or C-terminal amino acids added to the mature protein or for a polypeptide having internal amino acids (e.g., 2 or more polypeptide chains) added to the mature polypeptide. Such sequences can play a role in processing the protein from the precursor to mature form, can facilitate protein trafficking, can extend or reduce the half-life of the protein, or can facilitate manipulation of the protein for analysis or production. Generally, these additional amino acid sequences can be processed by cellular enzymes so as to be removed in situ from the mature protein.

The precursor protein having a mature form of the polypeptide bound to one or more prosequences may be in an inactivated form of said polypeptide. If the prosequence is removed, the inactivated precursor is generally activated. Some or all prosequences may be removed before activation. In general, such a precursor is called proprotein. Generally, the polynucleotide of the present invention can code for the mature protein, the mature protein and a leader sequence (which can also be called preprotein), a mature protein precursor having one or more prosequences which are not a leader sequence of the preprotein, or a preproprotein which is a proprotein precursor having one or more prosequences and a leader sequence to be removed during processing for producing the activated or mature form of the polypeptide.

Further, the present invention relates to a human TRPC7 polypeptide having the estimated amino acid sequence of SEQ ID NO:2. Also, the present invention relates to fragments, analogues and derivatives of these polypeptides. When the polypeptide of SEQ ID NO:2 is referred to, the terms "fragments", "derivatives" and "analogues" refer to polypeptides having substantially the same biological functions or activity as those of said polypeptide, i.e. to polypeptides having the functions of TRPC7. The analogues encompass e.g. proproteins which can be activated by cleavage of the part of proprotein, to produce active mature polypeptides. The polypeptides of this invention may be recombinant polypeptides, natural polypeptides or synthetic polypeptides, among which recombinant polypeptides are preferable. Fragments, derivatives or analogues of the polypeptide of SEQ ID NO:2 may be: (i) those wherein one or more amino acid residues are replaced by conserved or non-conserved amino acid residues (preferably conserved amino acids) and such replaced amino acid residues are encoded or not encoded by genetic code; (ii) those wherein one or more amino acid residues contain substituent groups; (iii) those wherein the mature polypeptide is fused to other compounds such as a compound (e.g., polyethylene glycol) increasing the half-life of the polypeptide; or (iv) those wherein additional amino acids such as a leader or secretary sequence, or a sequence used for purification of the mature polypeptide or proprotein sequences are fused to the mature polypeptide. Such fragments, derivatives and analogues are considered to be within the range of those skilled in the art on the basis of the description of this specification.

In this respect, a particularly preferable example of this invention includes polypeptides having the amino acid sequence of TRPC7 shown in SEQ ID NO:2, varieties, analogues, derivatives and fragments thereof, as well as varieties, analogues and derivatives of the fragments. In this respect, a particularly preferable example of this invention further includes polypeptides having the amino acid sequence of TRPC7, and varieties, analogues and derivatives thereof maintaining TRPC7 activity/functions, as well as varieties, analogues and derivatives of the fragments. Preferable varieties are differentiated from the subject by replacement of conserved amino acids. In such replacement, predetermined amino acids in the polypeptide are replaced by other amino acids having similar characteristics. Typical conservative replacement includes mutual replacement of aliphatic amino acids Ala, Val, Leu and Ile, mutual replacement of hydroxyl residues Ser and Thr, exchange of acidic residues Asp and Glu, replacement between amide residues Asn and Gln, exchange between basic residues Lys and Arg, and exchange between aromatic residues Phe and Tyr.

Those preferable in this respect are varieties, analogues and derivatives TRPC7 wherein a few amino acids or 5 to 10, 1 to 5, 1 to 3, 2, 1 or 0 amino acid in the amino acid sequence of the TRPC7 polypeptide in SEQ ID NO:2 have been replaced, deleted and/or added, as well as varieties, analogues and derivatives of said fragments. Among these, silent replacement, addition and deletion not changing the properties and activity of TRPC7 are particularly preferable. Conservative replacement is also particularly preferable in this respect. The most preferable example is a polypeptide having the unsubstituted amino acid sequence of SEQ ID NO:2. The polypeptide and polynucleotide of the present invention are provided preferably in an isolated form or a homogeneously purified form.

The polypeptide of the present invention includes the polypeptide of SEQ ID NO:2 (particularly the mature polypeptide) and polypeptides having at least 70% homology to the polypeptide of SEQ ID NO:2, more preferably polypeptides having at least 80 to 90% analogy (more preferably at least 90% homology) to the polypeptide of SEQ ID NO:2, most preferably at least 95% analogy (more preferably at least 95% homology) to the polypeptide of SEQ ID NO:2, and contains generally a portion containing at least 30 amino acids, more preferably at least 50 amino acids from such polypeptides. The analogy between 2 polypeptides is defined and measured as described above.

A fragment or a part of the polypeptide of the present invention is used to produce the full-length polypeptide. Accordingly, the fragment is used as an intermediate for production of the full-length polypeptide. A fragment or a part of the polynucleotide of the present invention is used for synthesis of the full-length polynucleotide of the present invention. The fragment may not be "independent", that is, it may not only be a part of other amino acids or of a polypeptide or fused thereto, but may be contained in a larger polypeptide to form a part or region thereof. If it is contained in a larger polypeptide, the fragment discussed here forms most preferably a single continuous region. However, a few fragments may be contained in a single larger polypeptide. For example, in a certain preferable example, the fragment is contained in a precursor polypeptide designed for expression in hosts. An example is a fragment of the TRPC7 polypeptide of the present invention having a heterogeneous pre- and propolypeptide regions fused to the N-terminal of the TRPC7 fragment and an additional region fused to the C-terminal of said fragment. Accordingly, a fragment as one mode in the meaning contemplated in the present specification refers to the part of a fusion polypeptide or fusion protein derived from TRPC7.

Typical examples of the polypeptide fragment of the present invention include those having a length of about 5 to 15, 10 to 20, 15 to 40, 30 to 55, 41 to 75, 41 to 80, 41 to 90, 50 to 100, 75 to 100, 90 to 115, 100 to 125 and 110 to 113 amino acids. The term "about" indicates that the mentioned range may be larger and/or smaller by several amino acids or 5, 4, 3, 2 or 1 amino acid residue. For example, about 40 to 90 amino acids mean the range of from 40 (several, 5, 4, 3, 2 or 1 amino acid residues to 90 (several, 5, 4, 3, 2 or 1 amino acid residues, that is, from 40 minus several amino acids to 90 plus several amino acids in a broader range to 40 plus several amino acids to 90 minus several amino acids in a narrower range. In this respect, it is preferable that the mentioned range is larger and/or smaller by 5 amino acids. It is more preferable that the mentioned range is larger and/or smaller by 3 amino acids. It is most preferable that the mentioned range is larger and/or smaller by 1 amino acid. In these respects, the most preferable fragments are those having a length of about 5 to 15, 10 to 20, 15 to 40, 30 to 55, 41 to 75, 41 to 80, 41 to 90, 50 to 100, 75 to 100, 90 to 115, 100 to 125 and 110 to 113 amino acids.

Particularly preferable fragments in the present invention are truncation varieties of TRPC7. The truncation varieties include TRPC7 polypeptides having the amino acid sequence in SEQ ID NO:2 or varieties or derivatives thereof. However, deletion of a series of continuous residues containing the N-terminal (that is, a continuous region, a part, a site) and/or a series of continuous residues containing the C-terminal, such as in double truncation varieties, is excluded. A particularly preferable fragment of the membrane-binding receptor of this invention includes a soluble form of a receptor consisting of an added transmembrane domain and a cytoplasmic domain-free extracellular domain or a receptor wherein an extracellular domain is directly fused to a cytoplasmic domain by deletion of a transmembrane region [13]. Generally, a fragment having a size in the above-described range, which is a preferable example of the truncation fragment, is particularly preferable among the fragments.

Further, a preferable example in this mode of the present invention is a fragment characterized by the structural or functional characters of TRPC7. In this respect, a preferable mode of the present invention includes an α-helix and an α-helix-forming region (α-region), a β-sheet and a β-sheet-forming region (β-region), a turn and a turn-forming region (turn region), a hydrophilic region, a hydrophobic region, an α-amphipathic region, a β-amphipathic region, a flexible region, a surface-forming region and a highly antigenic index region in TRPC7. A fragment particularly preferable in this respect is a fragment comprising a region of TRPC7 having some structural characters such as the structural characters described above. In this respect, fragments defined by about 10 to 20, about 40 to 50, about 70 to 90 and about 100 to 113 residues in SEQ ID NO:2, characterized by an amino acid composition having the characteristics of a turn region, a hydrophilic region, a flexible region, a surface-forming region and an antigenic index region are particularly preferable regions. Such regions are contained in a larger polypeptide or they themselves are preferable fragments in the present invention, as described above. The term "about" is used in the same meanings as described generally for the fragments.

A further preferable region is to transmit the activity of TRPC7. In this respect, the most preferable fragment is a fragment having the chemical, biological or other activities of TRPC7, including the one having similar or improved activities or reduced undesirable activities. In this respect, a fragment containing the region of a homologue in sequence and/or location to the active region of a relevant polypeptide such as TRP and human TRP. A particularly preferable fragment in this respect is the truncation mutant described above or a fragment consisting of transmembrane or extracellular domains. The fragment of this invention includes a fragment lacking in a transmembrane domain only and keeping at least its cytoplasmic domain or a fragment formed by fusion to at least another cytoplasmic domain [14]. In particular, the present invention relates to a polynucleotide coding for the fragment described above, a polynucleotide hybridizing with a polynucleotide coding for said fragment, in particular a polynucleotide hybridizing therewith under stringent conditions and a polynucleotide such as a PCR primer for amplifying said fragment. A preferable polynucleotide in this respect is a fragment corresponding to the preferable fragment described above.

In addition, the present invention relates to the polynucleotide, a vector containing the polynucleotide of the invention, host cells genetically manipulated by the vector of the invention and production of the polypeptide of this invention by recombinant techniques. The polypeptide of the invention can be expressed by genetically manipulating host cells for integration of the polynucleotide of the invention. For example, the polynucleotide can be integrated into host cells by well-known techniques such as infection, transduction, transfection, transvection and transformation. The polynucleotide can be integrated alone or in combination with other polynucleotides. Such other polynucleotides can be integrated independently or integrated together with, or by linking to, the polynucleotide of the invention. For example, the polynucleotide of this invention can be transfected into host cells along with another polynucleotide coding for a selectable marker, for example by co-transfection in mammalian cells and by a standard method for selection. In this case, the polynucleotide can be integrated stably in the genome of host cells.

In an alternative method, the polynucleotide can be linked to a vector containing a selectable marker for proliferation in a host. Said vector construct can be integrated into host cells by use of the techniques described above. In general, it is integrated as DNA in precipitates such as calcium phosphate precipitates or in the form of a complex with charged lipids into a plasmid vector. Electroporation can also be used to integrate the polynucleotide into hosts. When the vector is a virus, the virus can be packaged in vitro or integrated in package cells and the packaged virus can be used to transduce cells. The polynucleotide is prepared according to this mode of the present invention. A variety of techniques suitable for integrating the polynucleotide into cells are well-known and constitute a routine work for those skilled in the art. Such techniques are described in detail in [15], and this literature describes a large number of laboratory manuals showing the details of these techniques. According to this mode of this invention, the vector may be e.g. a plasmid vector, a single- or double-stranded phage vector or a single- or double-stranded RNA or DNA virus vector. Such a vector can be integrated as a polynucleotide, preferably DNA into cells by any known techniques for integrating DNA and RNA into cells. In the case of the phage and virus vector, the vector can be integrated preferably as a package or capsulated virus by well-known techniques for infection and transduction. The virus vector may be a replicating component or deficient in replication. In the latter case, generally viral proliferation occurs only when host cells are complemented.

The preferable vector in this respect is a vector for expression of the polynucleotide and polypeptide of the present invention. Generally, such vectors consist of a cis-acting regulatory region which is effective for expression in host cells and linked in an operable manner to the polynucleotide to be expressed. A suitable trans-acting factor is supplied by a host, by a complementing vector or by a vector itself after being integrated into a host. In an example preferable in this respect, the vector is subjected to specific expression. Such specific expression can be inducible expression or expression in only a certain type of cells and cell-specific expression or both inducible and cell-specific expression. Particularly preferable vectors among those inducible are vectors whose expression is inducible by an easily operative environmental factor such as temperature and nutritive additives. Various vectors suitable for this mode of this invention, including constitutional and inducible expression vectors for use in prokaryotic and eucaryotic hosts, are well known and routinely used by those skilled in the art.

The manipulated host cells can be cultured in a usual nutrient medium, and the medium can be specially modified to activate a promoter, to select a transformant or to amplify the gene. Culture conditions such as temperature, pH etc. used for expression and selection for host cells shall be suitable for expression of the polypeptide of this invention and evident to those skilled in the art. Various expression vectors can be used for expression of the polypeptide of this invention. Such vectors include chromosomes, episomes and viral inducible vectors, e.g. microbial plasmids, bacteriophage, yeast episomes, vectors derived from yeast chromosome elements, viruses such as Baculovirus, papovavirus, SV40, vaccinia virus, Adenovirus, fowlpox virus, pseudo-rabies virus and retrovirus, vectors derived from plasmids and genetic elements in bacteriophage, and vectors such as cosmid and phagimide, derived from a combination of the above. In general, any vectors suitable for maintaining the polynucleotide, multiplying and expressing it to produce the polypeptide can be used as expression vectors.

Suitable DNA sequences can be inserted into a vector by a wide variety of known and ordinary procedures. In general, a DNA sequence for expression and an expression vector are cleaved with one or more restriction endonucleases, and the resulting restriction fragments are ligated by T4 DNA ligase whereby the DNA sequence is ligated to the expression vector. The procedure for restriction and ligation used for this purpose is well-known to those skilled in the art and routinely carried out. The. DNA sequence in the expression vector is linked in an operable manner to a suitable expression regulatory sequence containing e.g. a promoter for directing mRNA translation. Typical examples of such promoters include λ-phage PL promoter, $E.$ $coli$ lac, trp and tac promoters, SV40 early and late promoters and retrovirus LTR. A large number of other promoters useful in the present invention are well-known and can be ordinarily used by those skilled in the art according to a method described in this specification and the examples.

In general, an expression construct has transcription initiation and termination sites, and its translation region possesses a ribosome-binding site for translation. A coding region in a mature transcript expressed by said construct contains the translation initiation codon AUG and the translation termination codon located respectively at the start and end of a polypeptide to be translated. In addition, the construct may contain regulatory regions for regulating and initiating expression. Generally, such sequences are manipulated by regulating transcription by a large number of procedures practiced in common. For example, a repressor-binding region and an enhancer are mentioned. Generally, a vector for multiplication and expression contains a selectable marker. The selectable marker gives phenotypic traits for selection of transformed host cells. A preferable marker includes, but is not limited to, dihydrofolate reductase or neomycin resistance for culture of eucaryotic cells and tetracycline or ampicillin resistance in $E.$ $coli$ and other microorganisms. A vector having the suitable DNA sequence, a suitable promoter and a regulatory sequence, as described above, is used to transform suitable hosts so as to permit the hosts to express the protein. Such a marker is also suitable for amplification. Alternatively, an additional marker may be contained for this purpose.

The suitable DNA sequence described in this specification, as well as a suitable promoter and other suitable regulatory sequences, are introduced into a suitable host by use of a wide variety of well-known methods suitable for expressing the desired polypeptide therein. Typical examples of suitable hosts include microbial cells such as $E.$ $coli$, Streptomyces and $Salmonella$ $typhimurium$ cells; eucaryotic cells such as yeast cells; insect cells such as Drosophila S2 and SHIRONAYOTO Sf9 cells; animal cells such as CHO, COS or Bowes melanoma cells; and plant cells. Various hosts for the expression construct are well-known and can be selected ordinarily by those skilled in the art for expression of the polypeptide according to the mode of this invention in this specification.

In particular, the present invention also encompasses recombinant constructs such as expressed constructs including one or more sequences described above in a broad range. The construct has a vector such as plasmid or viral vector in which the sequence of this invention is inserted in the normal or reverse direction. In a preferred mode of this invention, the construct further has a regulatory region containing a promoter linked in an operable manner to said sequence. A large number of suitable vectors and promoters are known to those skilled in the art and these are commercially available. Hereinafter, commercially available vectors are mentioned for illustrative purposes. Vectors preferably used in microorganisms include pQE70, pQE60 and pQE-9 (Qiagen), pBS vector, phage script vector, Bluescript vector, pNH8A, pNH16a, pNH18A and pNH46A (Stratagene), and ptrc99a, pKK223-3, pKK233-3, pDR540 and pRIT5 (Pharmacia). Preferable vectors for eucaryotic cells include pWLNEO, pSV2CAT, p0G44, pXT1 and pSG (Stratagene) and pSVK3, pBPV, pMSG and pSVL (Pharmacia). These are merely illustrative of a large number of well-known, commercially available vectors usable in the present invention, and other plasmids and vectors can also be used in the present invention insofar as they can be introduced into hosts and are suitable for maintained, proliferation and expressing the polynucleotide or polypeptide of the present invention.

The promoter region can be selected from any desirable genes by use of a vector containing a reporter transcription unit lacking in a promoter region, such as a chloramphenicol acetyl transferase (CAT) transcription unit, a downstream for a restriction site for introduction of a candidate promoter fragment, that is, a fragment capable of containing a promoter. It is well-known that when a vector with a fragment containing a promoter is introduced into an upstream region from a restriction site in CAT gene, CAT activity is generated and can be detected by standard CAT analysis. Vectors suitable for this purpose are well-known and easily available. Two examples of such vectors are pKK232-8 and pCM7. That is, the promoter for expression of the polynucleotide of this invention is well-known and is not only easily available but also easily obtainable by the method described above using a reporter gene. Known microbial promoters suitable for expression of the polynucleotide and polypeptide according to the present invention are $E.$ $coli$ lacI and lacZ promoters, T3 and T7 promoters, gpt promoter, λPR, PL promoter and trp promoter.

Known eucaryotic promoters suitable in this respect are CMV immediate early promoter, HSV thymidine kinase promoter, early and late SV40 promoter, retrovirus-derived LTR such as LTR from Rous sarcoma virus (RSV) and metallothionein promoter such as mouse metallothionein-I promoter. Selection of vectors and promoters suitable for expression in hosts is a well-known procedure, and techniques necessary for introduction of an expression vector and a vector into a host and expression thereof in the host are a routine work for those skilled in the art. The present invention also relates to host cells containing the construct described above. The host cells may be higher eucaryotic cells such as mammalian cells, lower eucaryotic cells such as yeast cells or prokaryotic cells such as microbial cells. Introduction of the construct into host cells can be conducted by calcium phosphate transfection, DEAE-dextran-mediated transfection, cationic lipid-mediated transfection, electroporation, transduction, infection etc. These methods are described in a large number of standard laboratory manuals such as [16].

The construct in host cells is used in a usual manner whereby the gene product encoded by the recombinant sequence can be produced. In an alternative method, the polypeptide of the present invention can be synthesized by an ordinary peptide synthesizer. The mature protein can be expressed under the control of a suitable promoter in mammalian cells, yeast, microorganisms or other cells. A cell-free translation system can also be used to produce such protein by use of RNA derived from the DNA construct of the invention. Suitable cloning and expression vectors for use in prokaryotic and eucaryotic hosts are described in [15].

Generally, a recombinant expression vector contains an origin of replication, a promoter derived from a high-expression gene directing transcription of a downstream structural sequence, and a selectable marker permitting isolation of vector-containing cells after exposure to the vector. A suitable promoter can be derived from a gene coding for a glycolytic enzyme such as 3-phosphoglycerate kinase (PGK), α-factor, acid phosphatase or heat shock protein. Suitable markers include an ampicillin resistance gene from *E. coli* and a trpl gene from *Saccharomyces cerevisiae*. Transcription of the DNA coding for the polypeptide of this invention in higher eucaryotic cells can be enhanced by inserting an enhancer sequence into the vector. The enhancer is a DNA cis-acting element of usually about 10 to 300 bp in length and acts on predetermined host cells to increase the transcriptional activity of the promoter. Examples include a SV40 enhancer downstream by 100 to 270 bp from the origin of replication, a cytomegalovirus early promoter enhancer, a polyoma enhancer downstream of the origin of replication, and an Adenovirus enhancer.

The polynucleotide of this invention coding for the heterologous structural sequence of the polypeptide of the invention is inserted generally by standard techniques into a vector so as to be linked for expression to the promoter in an operable manner. The polynucleotide is located such that the transcription initiation site is present suitably at the 5'-side for a ribosome-binding site. The ribosome-binding site is located at the 5'-side of AUG for initiating translation of the polypeptide to be expressed. In general, there is no open reading frame initiating at the initiation codon, usually AUG, and occurring between the ribosome-binding site and the initiation codon. In general, a transcription termination codon is present at the end of the polypeptide, and a polyadenylation signal and a transcription termination signal are located suitably at the 3'-terminal of the transcriptional region. To secrete the translated protein into an endoplasmic reticular lumen, a periplasmic space or the extracellular environment, suitable secretory signals can be integrated into the expressed polypeptide. These signals may be internal to the polypeptide or may be heterogeneous signals. The polypeptide may be expressed in a modified form such as fusion protein or may contain not only secretary signals but also a further heterologous functional region. For example, such a region can be added to additional amino acids, particularly to a charged amino acid region or to the N-terminal of the polypeptide, to improve stability and durability during purification and subsequent handling and storage. To facilitate purification, such a region can also be added to the polypeptide. Such a region can be removed before the final production of the polypeptide. In particular, addition of a certain peptide portion to the polypeptide for initiating secretion, improving stability and facilitating purification is well-known in this field and constitutes ordinary techniques.

Suitable prokaryotic hosts suitable for multiplying, keeping and expressing the polynucleotide and polypeptide of the present invention include *Escherichia coli, Bacillus subtilis* and *Salmonella typhimurium*. Various species such as the genera Pseudomonas, Streptomyces and Staphylococcus are also suitable hosts in this respect. Further, other hosts known to those skilled in the art can also be used. Typical but non-limiting examples of useful expression vectors for microorganisms comprise a selectable marker and a microbial origin of replication derived from a commercially available plasmid consisting of genetic elements of pBR322 (ATCC37017) as a well-known cloning vector. Such commercial vectors include e.g. pKK223-3 (Pharmacia Fine Chemicals, Uppsala, Sweden) and GEM1 (Promega Biotec, Madison, Wis., USA). In these vectors, the "major chain" of pBR322 is combined with a suitable promoter and the structural sequence to be expressed. Following the transformation of a suitable host strain, the host strain is proliferated to suitable cell density. When a selected promoter can be introduced, it is introduced in a suitable means (e.g., temperature shift or exposure to a chemical agent for introduction), and the cells are cultured for an additional period of time. Then, the cells are harvested typically by centrifugation and then disrupted by a physical or chemical means, and the resulting crude extract is kept for further purification. Microbial cells used for expression of the protein can also be disrupted by any usual techniques including repetition of freezing and thawing, sonication, mechanical disruption and use of a cell lysing agent. Such techniques are also known to those skilled in the art.

A wide variety of mammalian cell culture systems can also be similarly used for expression. Examples of mammalian cell culture systems include, but are not limited to, C127, 3T3, CHO, HeLa, human renal 293 and BHK cell lines and ape renal fibroblast COK-7 line [17]. The mammalian expression vectors consist of an origin of replication, a suitable promoter, an enhancer, some necessary elements such as a ribosome-binding site, a polyadenylation site, a splice donor, an acceptor site and a transcription termination sequence, as well as a 5'-flanking non-transcriptional sequence necessary for expression. In a preferable example, a DNA sequence derived from SV40 splice site and SV40 polyadenylation site is used as a necessary non-transcriptional genetic element. The TRPC7 polypeptide can be recovered and purified from a culture of recombinant cells by well-known techniques such as ammonium sulfate or ethanol precipitation, acid extraction, anion- or cation-exchange chromatography, phosphocellulose chromatography, hydrophobic interaction chromatography, affinity chromatography, hydroxyapatite chromatography and lectin chromatography. High performance liquid chromatography (HPLC) is used most preferably for purification. If the polypeptide is denatured during isolation and/or purification, known techniques for protein regeneration can be used to restore its active conformation. The polypeptide of the present invention includes natural purified polypeptides and chemically synthesized polypeptides, as well as polypeptides produced by recombinant techniques from e.g. prokaryotic or eucaryotic hosts such as microorganisms, yeast, higher plants, insects and mammalian cells. Depending on the host used in the procedure for production of the recombinant, the polypeptide of the present invention can be glycosylated or non-glycosylated. Further, the polypeptide of this invention may contain a modified initiation methionine residue in some cases as a result of the method of host intervention. The TRPC7 polynucleotide and polypeptide can be used according to the present invention for various uses, particularly for uses where TRPC7 is chemically and biologically used. Further uses are directed to diagnosis and therapy of insufficiency in cells, tissues and organs.

Further, the present invention relates to use of TRPC7 polynucleotide for detection of complementary polynucleotides for use as a diagnostic reagent. Detection of TRPC7 mutants accompanying malfunctions provides diagnosis of bipolar affective disorder caused by deficient expression, excessive expression or altered expression of TRPC7, or a diagnostic tool which can be added to the diagnosis. Individuals having mutations in human TRPC7 gene can be detected at the DNA level by various techniques. The nucleic acid for diagnosis can be obtained from patient's cells in blood, urine, saliva or samples in tissue biopsy or autopsy. Genomic DNA can be used for direct detection or can be enzymatically amplified by PCR [18] or any other amplification method before analysis. Similarly, RNA or cDNA can also be used. For example, deletion and insertion can be detected due to a change in the size of an amplification product relative to the normal genotype. Point mutation can be identified by hybridizing the amplified DNA with radioisotope-labeled TRPC7 RNA or radioisotope-labeled antisense DNA sequence. Completely paired sequences can be distinguished from a mismatched double helix by digestion with RNase A or due to a difference in melting temperature.

The difference in sequence between the control gene and the gene having a mutation can be shown directly by DNA sequencing. Further, the specified DNA segment can be detected by use of the cloned DNA segment as a probe. The sensitivity of these methods can be enhanced greatly by suitably using PCR or other amplification methods. For example, a sequencing primer is used together with a double-stranded PCR product generated by modified PCR or with a single-stranded template molecule. Sequencing can be carried out in a usual manner using a radioisotope-labeled nucleic acid or by an automatic sequencing procedure using a fluorescent tag. In a genetic test based on a difference in DNA sequence, this difference can be detected by a change in the mobility of a DNA fragment in gel by electrophoresis with or without a denaturing agent. Deletion and insertion of a small sequence can be visualized by high-separation gel electrophoresis. DNA fragments of different sequences can be distinguished from one another in a modified formamide gradient gel where the mobility of different DNA fragments in the gel is varied depending on their specific or partial melting temperatures [19]. A change at a specific position in the sequence can also be revealed by nuclease protection analysis, for example RNase and SI protection or chemical cleavage [20]. Detection of the specific DNA sequence can be conducted by hybridization, RNase protection, chemical cleavage, direct sequencing or use of restriction enzymes ( e.g., restriction fragment length polymorphism (RFLP)) and Southern blotting of genomic DNA.

Further, the present invention relates to diagnostic analysis for detection of expression level of TRPC7 protein in cells and tissues. Such analysis may be either quantitative or qualitative. That is, the diagnostic analysis of this invention for detecting excessive expression of TRPC7 protein as compared with a normal control tissue sample can be used for detection of the presence of bipolar affective disorder. Analytical techniques usable for measuring the level of a protein such as the TRPC7 protein of the present invention are well-known to those skilled in the art. Such analytical methods include radioimmunoassays, competitive binding assays, Western blotting techniques and ELISA assays. In particular, ELISA assays are preferable. The ELISA assays involve preparation of an antibody preferably a monoclonal antibody specific to TRPC7 protein. Further, a labeled antibody binding to said monoclonal antibody is generally prepared. Said reporter antibody is bound to a detectable reagent such as a radioactive, fluorescent or enzymatic reagent, for example horseradish peroxidase as described herein.

For conducting ELISA, a sample suspected of containing TRPC7 protein is removed from a host and then incubated on a solid carrier e.g. a 96-well microplate binding to said protein in the sample, whereby the protein is adsorbed onto a well in the plate. Any of the free protein-binding site on the well is coated by incubation with unspecific protein such as bovine serum albumin. Then, a monoclonal antibody is incubated in the well. Meanwhile, the monoclonal antibody binds to TRPC7 protein previously bound to the well in the microtiter plate. The unbound monoclonal antibody is washed away with a buffer. A labeled antibody bound to horseradish peroxidase is put to the well and bound to the monoclonal antibody previously bound to TRPC7 protein. Then, the unbound labeled antibody is washed away. Then, a reagent for measurement of peroxidase activity containing a substrate for colorimetry is added to the well. The immobilized peroxidase bound via the primary and secondary antibodies to TRPC7 protein forms a coloring reaction product. The coloration generated during a predetermined time is indicative of the amount of TRPC7 protein present in the sample. The quantitative result is obtained typically by comparison with a standard curve. Competitive analysis can also be used, and a TRPC7-specific antibody is bound to a solid carrier, and labeled TRPC7 protein and a sample derived from a host are added to the solid carrier. The amount of the label bound to the solid carrier can be correlated with the amount of TRPC7 protein in the sample.

The polypeptide of the present invention, fragments thereof or other derivatives thereof, or analogues thereof, or cells expressing them can be used as an immunogen for production of antibodies against them. These antibodies are e.g. monoclonal and polyclonal antibodies. The present invention encompasses chimeral, single-stranded and humanized antibodies, as well as Fab fragments or products in a Fab expression library. Various methods known in this field can be used for production of these antibodies and fragments. Antibodies raised against a polypeptide with the sequence of this invention can be obtained by directly injecting or administering said polypeptide to animals other than humans. The resulting antibodies bind to the polypeptide itself. The sequence coding for only a fragment of the polypeptide can also be used in this manner for production of antibodies binding to the entire natural polypeptide. Such antibodies can be used for isolation of the polypeptide from tissues expressing the polypeptide. The monoclonal antibodies can be prepared by use of techniques of providing antibodies produced by continuous cell line culture, and these techniques are well-known to those skilled in the art. The method of producing monoclonal antibodies includes the hybridoma method [21], the trioma method, the human B cell hybridoma method [22], and EBV-hybridoma method [23].

The techniques described for production of single-stranded antibodies [24] can be used to produce single-stranded antibodies against the polypeptide of this invention. Further, transgenic mice or other creatures, for example other mammals can be used to express the humanized antibodies of this invention. The above antibodies can be used for isolation or identification of clones expressing said polynucleotide, and the antibody is bound to a solid carrier for isolation and/or purification so that the polypeptide of this invention can be purified by affinity chromatography. Although use of the antibodies against TRPC7 protein is not particularly limited, they can be used to inhibit bipolar affective disorder.

TRPC7 can be used for isolation of interacting proteins, and this interaction can be a target of interference. An inhibitor of protein-protein interaction between TRPC7 and another factor leads to the development of pharmaceutical preparations for regulation of TRPC7 activity. Thus, the present invention also provides a method of identifying a molecule binding to TRPC7. A gene coding for a protein with the molecule binding to TRPC7 can be identified by a large number of known methods such as ligand panning and FACS sorting. Such methods are described in many laboratory manuals such as [25]. For example, a yeast hybrid system provides a method of detection of in vivo interaction between a first test protein and a second test protein. This method is disclosed in [26], and the reagent is available from Clontech and Stratagene. Briefly, TRPC7 cDNA is fused to a DNA-binding domain in Gal4 transcription factor and expressed in yeast cells. A cDNA library member obtained from cells of interest is fused to a trans-activating domain in Gal4. A cDNA clone expressing a protein capable of interacting with TRPC7 brings about reconstruction of Gal4 and trans-activation of a reporter gene such as Gal1-lacZ.

In an alternative method, there is screening of λgt11 or λZAP (Stratagene) or an equivalent cDNA expression library by recombinant TRPC7. The recombinant TRPC7 protein or its fragments are fused to a small peptide tag such as FLAG, HSV or GST. The peptide tag can have a convenient phosphorylation site for kinases such as cardiac muscular creatine kinase or may be biotinylated. The recombinant TRPC7 can be phosphorylated with 32P or can be detected without any label by an antibody against streptavidin or the tag. A λgt11 cDNA expression library is prepared from cells of interest and incubated with recombinant TRPC7 and washed to isolate cDNA clones interacting with TRPC7. Such a method is a routine work for those skilled in the art [15]. Another method is screening of an mammalian expression library. In this method, cDNA is cloned between a mammalian promoter and a polyadenylation site in a vector and used to transfect COS or 293 cells transiently. After 48 hours, the cells are immobilized and washed, and then the cells are incubated with labeled TRPC7 to detect the bound protein. In a preferred example, TRPC7 is iodized and the bound TRPC7 is detected by autoradiography [27][28]. In this method, a cDNA pool containing cDNA coding for the binding protein of interest is selected, and each pool is divided followed by repeating a cycle consisting of transient transfection, binding and autoradiography, whereby the cDNA of interest can be isolated. In a separate method, an entire cDNA library is transfected into mammalian cells and the cells are panned with a vessel containing TRPC7 bound to a plate, whereby the cDNA of interest can be isolated. After washing, the bound cells are lyzed to isolate plasmid DNA which is then amplified in microorganisms and subjected repeatedly to a cycle of transfection and panning until a single cDNA clone is obtained [29][30]. In the case where the bound protein is secreted, once binding or neutralization analysis is established such as in analysis of a supernatant from transiently transfected cells, the cDNA can be obtained by the same pool method. A general method for screening the supernatant is disclosed in [31].

Another method involves isolation of a protein interacting directly with TRPC7 from cells. A fusion protein of TRPC7 with GST or a small tag is prepared and immobilized onto beads. An extract of a biosynthetically labeled or unlabeled extract is prepared from cells of interest, incubated with the beads and washed with a buffer. The protein interacting with TRPC7 is specifically eluted from the beads and analyzed by SDS-PAGE. Data on the primary amino acid sequence of the binding partner can be obtained by microsequencing. If desired, the cells may be treated with a reagent for inducing a functional response such as tyrosine phosphorylation of the cellular protein. Examples of such a reagent are growth factors or cytokines such as interleukin-2. Another method is immuno-affinity purification. Recombinant TRPC7 is incubated with a labeled or unlabeled cellular extract and immuno-precipitated with anti-TRPC7 antibody. The immuno-precipitates are recovered with protein A-Sepharose and analyzed by SDS-PAGE. The unlabeled protein is labeled by biotinylation and detected with streptavidin on SDS gel. The protein of the binding partner is analyzed by microsequencing. Further, a known standard biochemical purification process may be used before microsequencing.

A further other method is screening of a binding partner in a peptide library. By use of tagged or leveled recombinant TRPC7, a peptide interacting with the TRPC7 is selected from a peptide or phosphopeptide library. By sequencing of the peptide, a consensus peptide sequence which can be found in the interacting protein can be identified. The TRPC7-binding molecule and the above-described estimated binding partner identified by any of these methods or other known methods can be used in the analytical method of this invention. Analysis of the presence of a TRPC7/binding partner complex can be conducted in e.g. a yeast hybrid system or by ELISA or immunoassays using a specific antibody to said complex. A decrease in the amount of the complex in the presence of a test substance interfering or inhibiting formation of the TRPC7/binding partner complex, relative to the control in the absence of the test substance, is measured. Analysis of free TRPC7 or the binding partner can be conducted by ELISA or immunoassays using a specific antibody, or by incubating radioisotope-labeled TRPC7 with cells or cell membranes and then separating them by centrifugation or through a filter. An increase in the amount of free TRPC7 or the free binding partner in the presence of a test substance interfering or inhibiting formation of the TRPC7/binding partner complex, relative to the control in the absence of the test substance, is measured. The polypeptide of this invention can also be used for evaluation of the ability of the TRPC7-binding molecule to bind to TRPC7 in cells or cell-free preparations.

TRPC7 according to this invention also has a calcium channel action and can also be used in a method of screening a compound for activation (agonist) or inhibition (antagonist) of the calcium channel action of TRPC7. Generally, such screening procedures include production of cells suitable for expressing the calcium channel polypeptide of the present invention on the surfaces of the cells. Such cells include cells from mammals, yeast, Drosophila or *E. coli*. In particular, the polynucleotide of this invention coding for calcium channels can be used to transfect cells thereby expressing TRPC7. Cells expressing calcium channels are brought into contact with a test compound, and inhibition of binding, stimulating or functional response is observed. One of such screening procedures involves use of melamine cells transfected for expressing the TRPC7 of this invention. Such screening technique is described in [32]. In one example, this technique is used for screening a compound inhibiting the activation of the calcium channel polypeptide of this invention, by bringing melamine cells expressing calcium channels into contact with both a ligand and a compound to be screened. The inhibition of signal generation by the ligand indicates that the compound is a potential antagonist for calcium channels, that is, the compound inhibits the activation of calcium channels. This technique can also be used for screening a compound activating calcium channels by bringing such cells into contact with a compound to be screened and determining whether the compound generates a signal or not, that is, whether the compound activates calcium channels or not.

Another screening technique involves use of cells (e.g. transfected CHO cells) expressing TRPC7 in a system where the change in extracellular pH caused by activation of calcium channel is measured [33]. In this technique, a test compound can be brought into contact with cells expressing the calcium channel polypeptide of this invention. Then, whether said potential compound activates or inhibits calcium channels is determined by measuring a second messenger response such as signal transduction or a change in pH. Another screening technique involves introducing TRPC7-coding RNA into oocytes from Xenopus and expressing calcium channels transiently. Then, the oocytes are brought into contact with a ligand and a compound to be screened. The inhibition of activation of calcium channels is measured by detecting the signal of calcium, proton or other ions, for example in the case of screening of a compound suspected of inhibiting the activation of calcium channels. Another screening technique involves expression of TRPC7, and calcium channels bind to phospholipase C or D. Typical examples of such cells include, but are not limited to, endothelial cells, smooth muscular cells and fetal renal cells. This screening can be conducted by detecting the activation of calcium channels or the inhibition of activation of calcium channels, from the secondary signal of phospholipase, as described above.

The other method includes screening an antagonist, that is, a compound inhibiting the activation of the calcium channel polypeptide of this invention, which comprises measuring the inhibition of binding of a labeled ligand to cells having calcium channels on the surfaces of the cells. Such a method involves transfecting eucaryotic cells with DNA coding for TRPC7 to permit the cells to express calcium channels thereon. The cells are brought into contact with a test compound in the presence of a labeled known ligand. The ligand can be labeled with e.g. a radioisotope. The amount of the ligand bound to calcium channels is determined by measuring e.g. the radioactivity of the transfected cells or of a membrane therefrom. When the compound is bound to calcium channels, the binding of the labeled ligand to calcium channels is inhibited so that a decrease in the labeled ligand thereon is detected. Another method includes screening of a TRPC7 inhibitor by measuring the inhibition or stimulation of accumulation of TRPC7-mediated cAMP and/or adenylate cyclase. Such a method involves transfecting eucaryotic cells with the TRPC7 gene to express calcium channels on the surfaces of the cells. Then, the cells are exposed to a potential antagonist in the presence of TRPC7 and the amount of cAMP accumulated is determined. Once the potential antagonist binds to calcium channels, that is, once the binding of TRPC7 is inhibited, the level of TRPC7-mediated cAMP or adenylate cyclase activity is decreased or increased.

Another method of detecting the agonist or antagonist of the invention for calcium channels includes techniques based on yeast [34]. The present invention provides a method of determining whether an unknown ligand whose ability to bind to TRPC7 calcium channels is not revealed binds to such calcium channels or not. This method comprises bringing mammalian cells expressing TRPC7 calcium channels into contact with a ligand under the conditions where the ligand can bind to TRPC7 calcium channels and then detecting the presence of the ligand bound to the calcium channels thereby determining whether the ligand binds to TRPC7 calcium channels or not. The above-described system where the agonist and/or the antagonist are measured can also be used for measurement of a ligand binding to calcium channels. Examples of potential TRPC7 calcium channel antagonists include antibodies or sometimes oligonucleotides which bind to calcium channels but do not inhibit activation of calcium channels due to a second messenger response. Further, the potential antagonists include proteins related closely to ligands for TRPC7 calcium channels, that is, fragments of the ligands, and such proteins lose biological functions and generate no response upon binding to TRPC7 calcium channels.

The potential antagonists include antisense constructs prepared by use of antisense techniques. The antisense techniques can be used to control formation of a triple helix or gene expression by antisense DNA or RNA, and both of the methods are based on binding of the polynucleotide to DNA or RNA. For example, the 5'-coding region of a polynucleotide sequence coding for the mature polypeptide of the invention is used to design antisense RNA oligonucleotide of about 10 to 40 bp in length. The DNA oligonucleotide is designed to be complementary (triple helix) to the region of a gene involved in transcription [35][36][37], whereby transcription and production of TRPC7 calcium channels are prevented. The antisense RNA oligonucleotide forms a hybrid with mRNA in vivo to block the transcription of the mRNA molecule into TRPC7 calcium channels (antisense) [38][39]. The oligonucleotide described above can be derived from cells and can express antisense RNA or DNA in vivo so as to inhibit production of TRPC7 calcium-channels. The other potential antagonist is a small molecule which binds to TRPC7 calcium channels to make the approach of the channels to ligands difficult, thus inhibiting normal biological activity. Examples of the small molecule include, but are not limited to, small peptides and peptide-like molecules. The other potential antagonist includes TRPC7 calcium channels in a soluble form, for example fragments of calcium channels, and these prevent ligands from binding to, and interacting with, membrane-bound TRPC7 calcium channels.

TRPC7 calcium channels are ubiquitous in mammalian hosts and participate in many biological functions including many pathogenic conditions. Accordingly, it is desired to find compounds and reagents which can stimulate TRPC7 calcium channels and simultaneously inhibit the functions of TRPC7 calcium channels. Generally, agonists of TRPC7 calcium channels can be used for treatment or prevention of bipolar affective disorder. Antagonists of TRPC7 can be used for various treatments or prevention of bipolar affective disorder. The present invention further provides a method of treating abnormal conditions related to excessive TRPC7 activity, which comprises administering said inhibiting compound (antagonist) along with a pharmaceutically acceptable carrier in an effective dose to inhibit activation of TRPC7 calcium channels by blocking the binding of ligands to the channels or by inhibiting a secondary signal, thus reducing the abnormal symptoms. In addition, the present invention provides a method of reducing abnormal symptoms related to TRPC7 and deficient expression of its activity, which comprises administering an effective dose of a compound (agonist) activating the calcium channel polypeptide of the invention described above into a patient along with a pharmaceutically acceptable carrier thereby reducing the abnormal symptoms.

TRPC7 in a soluble form and a compound activating or inhibiting such calcium channels can be used in combination with a pharmaceutical carrier. Such a composition comprises a therapeutically effective dose of the polypeptide or the compound and a pharmaceutically acceptable carrier or excipient. The carrier includes, but is not limited to, a saline solution, a buffered saline solution, dextrose, water, glycerol, ethanol and a combination thereof. The formulation should be adapted to the administration method. Selection of a suitable carrier for the administration method is a routine work for those skilled in the art. Further, the present invention provides a pharmaceutical pack or a kit comprising one or more vessels filled with one or more ingredients described above in the pharmaceutical composition of this invention.

The polypeptide and other compounds according to the present invention can be used alone or in combination with other compounds having pharmaceutical effects. The pharmaceutical composition is administered in an effective and convenient method via topical, oral, anal, vaginal, intravenous, intraperitoneal, intramuscular, hypodermal, nasal or intradermal routes. The pharmaceutical composition is administered in an effective dose for treatment and prevention of the specific disease for which it is efficacious. In general, the pharmaceutical composition is administered in a dose of at least 10 $\mu$g/body weight kg, and in almost cases, it is administered daily in a dose of less than about 8 mg/body weight kg. Preferably, the dose is about 10 $\mu$g to about 1 mg/body weight kg in consideration of the administration route, symptoms etc. As is evident, the optimum dose shall be determined by a standard method for individual therapeutic modality and the disease for which the composition is efficacious, in consideration of the disease, severity, administration route and complications.

According to the present invention, the TRPC7 polynucleotide, the polypeptide, the agonist and antagonist as a polypeptide can be used in a therapeutic modality often called "gene therapy" by expressing such polypeptides. That is, e.g. cells from a patient are genetically manipulated ex vivo with the polynucleotide such as DNA or RNA coding for the polypeptide. Then, the genetically manipulated cells are given to a patient to be treated with the polypeptide. In this example, the cells can be genetically manipulated ex vivo with e.g. a retrovirus plasmid vector containing RNA coding for the polypeptide of this invention. Such methods are well-known in this field, and use of these methods in this present invention would be evident from the description of this specification. Similarly, the cells can be genetically manipulated in vivo whereby the polypeptide is expressed in vivo by a procedure known in this field. For example, the polynucleotide of this invention can be manipulated so as to be expressed in a transcription-deficient retrovirus vector, as described above. The retrovirus expression construct is isolated and introduced into packaging cells transduced with a retrovirus plasmid vector containing RNA coding for the polypeptide of the present invention whereby the packaging cells can newly produce infectious viral particles containing the gene of interest. Such producing cells are introduced into patients and the cells are manipulated in vivo to produce the polypeptide in vivo. These and other methods for administration of the polypeptide of this invention would be evident to those skilled in the art on the basis of the teachings of this invention.

Retroviruses from which the retrovirus plasmid vectors can be derived include, but are not limited to, Moloney murine leukemia virus, spleen necrosis virus, Rous sarcoma virus (RSV), Harvey sarcoma virus, chicken leukemia virus, gibbon leukemia virus, human immunodeficiency virus, Adenovirus, bone marrow vegetative sarcoma virus and breast cancer virus. In a preferable mode, the retrovirus plasmid vector is induced from Moloney murine leukemia virus. Such a vector contains one or more promoters for expression of said polypeptide. Suitable usable promoters include, but are not limited to, retrovirus LTR, SV40 promoter and human cytomegalovirus (CMV) promoter [40]. As non-limiting examples, eucaryotic promoters including histone, RNA polymerase III and $\beta$-actin promoter can also be used. Further, usable virus promoters include, but are not limited to, Adenovirus promoter, thymidine kinase (TK) promoter and B19 parvovirus promoter. Selection of suitable promoters would be evident to those skilled in the art on the basis of the teachings of this specification.

The nucleic acid sequence coding for the polypeptide of this invention is placed under the control of a suitable promoter. Suitable usable promoters include, but are not limited to, Adenovirus promoters such as Adenovirus main late [literal translation] promoter; heterologous promoters such as cytomegalovirus (CMV) promoter; RS virus (RSV) promoter; inducible promoters such as MMT promoter and metallothionein promoter; heat shock promoter; albumin promoter; ApoAI promoter; human globulin promoter; viral thymidine kinase promoters such as herpes simplex thymidine kinase promoter; retrovirus LTR ( including the modified retrovirus LTRs described above); $\beta$-actin promoter and human growth hormone promoter. Further, the promoter may be a natural promoter capable of regulating a gene coding for the polypeptide. The retrovirus plasmid vector is used for transduction of a packaging cell line to form a producing cell line. Examples of packaging cells capable of transfection include, but are not limited to., PE501, PA317, $\phi$-2, $\phi$-AM, PA12, T19-14X, VT-19-17-H2, $\phi$CRE, $\phi$CRIP, GP+E-86 and GP+envAm12, as well as DNA cell lines described in [41]. The vector can be transduced into packaging cells by any methods known in the art. Such methods include, but are not limited to, electroporation, use of liposomes, and precipitation with CaPO4. Alternatively, the retrovirus plasmid vector can be enclosed in liposomes or bound to lipids, and then administered into hosts.

The producing cell lines generate infectious retrovirus vector particles containing a nucleotide sequence coding for said polypeptide. Such retrovirus vector particles can be used for transduction into eucaryotic cells in vitro or in vivo. The transduced eucaryotic cells express the nucleotide sequence coding for said polypeptide. The transduced eucaryotic cells include, but are not limited to, fetal stem cells, fetal cancer cells, hematopoietic stem cells, hepatocytes, fibroblasts, myoblasts, keratinocytes, endothelial cells and bronchial epithelial cells.

Hereinafter, the present invention is described in more detail by reference to the examples. The following examples are shown merely for illustrative purposes by specific examples. These illustrations describe certain specific modes of this invention, but are not intended to limit the scope of this invention. Unless otherwise specified, all the examples are carried out by ordinary standard techniques well-known to those skilled in the art. The "part" or "amount" in the examples below are expressed on a weight basis unless otherwise noted. Size separation of fragments in the examples below is conducted by standard techniques using agarose and polyacrylamide gel unless otherwise noted [15][42].

1. Libraries for Preparation of Contig and Screening

Two different genomic DNA libraries were used for screening. That is, the libraries are chromosome 21-specific KU21 cosmid library and BAC (bacterial artificial chromosome) library.

The human chromosome 21-specific KU21 cosmid library (6-fold coverage of chromosome 21) consisting of 10,624 clones, which was prepared from a sorted single human chromosome 21, was used [43][44][45]. For screening of this library, a high density replica (HDR) filter containing 1,536 clones from sixteen 96-well plates was prepared followed by screening by hybridization with the HDR filter. Isolation of cosmid DNA from E. coli made use of an automatic plasmid extraction robot PI-100. The DNA fragment excised from the gel was used as a probe for preparation of cosmid contig. 44 cosmid clones were isolated, and these clones were used for next working. As a result, 86 cosmid clones were obtained and these clones were divided whereby 2 contigs were obtained. By reference to a map of, 405-kb cosmid contig, in the same region prepared by restriction enzyme Hind III mapping [46], the length of the contig and the length of a gap between the contigs were estimated. The gap between the contigs was filled with LLNL cosmid clones Q1B4 and Q5B10.

For elongation of the contig, a BAC vector capable of cloning a longer DNA, fragment than cosmid was utilized [47]. This library has an average ,insert size of 110-kb and covers 3-fold, entire genome. A high density replica (HDR) filter containing 3,072 clones was prepared followed by screening by hybridization with the HDR filter. Five BAC clones were obtained from the BAC library, and 520-kb cosmid/BAC contig was finally constructed (FIG. 1).

2. Exon Trapping

For exon trapping, an Exon Trapping System (GIBCO BRL) was used. After the cosmid/BAC clone was partially digested with Sau3AI, the BAC clone was subcloned into pSPL3 cleaved with BamH I, and the cosmid clone was subcloned into pSPL3Cp cleaved with BamH I. After transformation of E. coli DH10B, the BAC clone was cultured overnight in an LB plate containing ampicillin, while the cosmid clone was cultured overnight in an LB plate containing chloramphenicol. These clones were harvested and plasmid DNA was extracted. The plasmid DNA was transduced into COS-7 cells by use of Lipofect AMINE (GIBCO BRL). After 36 hours, entire RNA was extracted from the COS-7 cells, cDNA was synthesized by a reverse transcriptase, and PCR using vector-specific primers was conducted. The PCR product was subcloned in pAMP10 vector by uracil DNA glyosidase (UDG) and introduced into E. coli DH10B. Finally, 22 exons were obtained, and these exons were amplified by PCR using vector-specific primers and then subjected to sequencing.

3. Sequencing of the Exons

The trapped exons were amplified directly from each colony by PCR using vector-specific primers. Sequencing was carried out by the dideoxy terminator method using a Dye Deoxy Terminator Cycle Sequencing Kit (Perkin Elmer). After the reaction, the sample was purified by a QIAquick Nucleotide Removable Kit (QIAGEN) to remove the unreacted dye deoxy terminator. For DNA nucleotide sequencing, an automatic fluorescence DNA sequencer (model 373A, ABI) was used. The sizes of these exons were in the range of 36 bp to 240 bp.

4. Searching for Homology

All the determined nucleotide sequences of the exons were input to a work station (SPARC Station produced by SUN) and each exon in the data base was examined for homology using a FASTA program [48] to determine overlapped sequences among the exons. Homology among nucleotide sequences from which the overlapped sequences had been removed and homology among amino acid sequences deduced therefrom were examined by use of BLASTN and BLASTX retrieval for GenBank/EMBL/DDBJ [49]. By examination of their homology in the DNA database, it was found that 6 exons were derived from known genes (PFKL, TMEM1) located in this region. Two exons (HC21EXc2, HC21EXc13) mached with exons 2 and 3 in the PFKL gene [50], and 4 exons (HC21EXb9, HC21EXb22, HC21EXb37, HC21EXb68) mached with the cDNA of the TMEM1 gene [51]. The other 16 exons were considered to be derived from a novel gene.

5. PCR Screening of cDNA Library

A pair of exon-specific oligo DNAs were used as primers for PCR. Six different human cDNA libraries from fetal brain (HL3003a), fetal liver (HL1005), liver (HL1001b), fetal heart (HL3018a), retina (HL1132a) and hippocampus (HL1028b) (Clontech Ltd.) were screened.

A suitable host (E. coli strain) was infected with about $10^8$ phage particles (corresponding to about $2 \times 10^5$ to $2 \times 10^6$ clones), the phages were multiplied and the phage DNA was isolated by the liquid lysate method [15]. 20 ng phage DNA corresponding to about $4 \times 10^8$ phages was used in PCR reaction under the following reactions. 1×buffer [50 mM KCl, 10 mM Tris-HCl pH 8.3, 1.5 mM $MgCl_2$, 0.001% (w/v) gelatin], 0.2 mM dNTPs, 0.25 U AmpliTaq DNA polymerase (Perkin-Elmer Ltd.) and 0.5 mM exon-specific primers were added to 10 ml reaction system, and 35 cycles of PCR were conducted under the conditions of 94° C. for 30 seconds, 55 to 65° C. (optimum temperature of the exon-specific primers) for 30 seconds and 72° C. for 30 seconds. The amplified exon fragments were electrophoressed in 2% agarose gel. The results are shown in Table 1.

TABLE 1

Expression of 13 exons in different human tissues

| Exon | cDNA library* |
|---|---|
| HC21EXc5 | fB, fH, Hi, Re |
| HC21EXc11 | fB, fH, fL, Hi, L, Re |
| HC21EXc16 | fB, fH, fL, Hi, L, Re |
| HC21EXc19 | fB, fH, Hi, Re |
| HC21EXc31 | fB |
| HC21EXc32 | Hi, L |
| HC21EXc65 | fH |
| HC21EXc111 | fH, Re |
| HC21EXc122 | none |
| HC21EXc132 | fB, Hi, Re |

TABLE 1-continued

Expression of 13 exons in different human tissues

| Exon | cDNA library* |
|---|---|
| HC21EXc143 | Re |
| HC21EXc145 | fB, fH, fL, Hi, L, Re |
| HC21EXb15 | fB, fH, Hi, L, Re |

*fB: fetal brain, fH: fetal heart, fL: fetal liver, L: liver, Re: retina, Hi: hippocampus 6. Isolation of cDNA of a Novel Gene As shown in Table 1, HC21EXc132 out of the 16 exons had been expressed in the fetal brain, hippocampus, and retina cDNA libraries by PCR screening of the various cDNA libraries using exon-specific primers. To isolate cDNA containing this exon, the human fetal brain cDNA library was screened by using exon HC21EXc132 as a probe, and clone 7-1 was obtained from the human fetal brain cDNA library.

Meanwhile, genome sequencing of 2 cosmids (D99F9, D107C4) and 1 BAC (KB68A7) was conducted. The nucleotide sequences of BAC DNA (KB68A7) and cosmid DNAs (D99F9, D107C4) containing the TRPC7 gene were determined by the shot gun method. The repetitive sequences were removed from the entire nucleotide sequences, and the remaining nucleotide sequences were subjected to BLASTN retrieval for Genbank/EMBL/DDBJ to analyze their homology.

The sequence data were analyzed by an exon predicting program GRAIL, and PCR primers were designed on the basis of the data. PCR was conducted where DNA prepared from a cDNA library of caudate nucleus (literal translation) was used as a template, whereby 3 PCR products P2, P3 and P4 were obtained. Further, human fetal brain and caudate nucleus cDNA libraries were screened with the PCR product P4 as a probe in order to elongate the 3'-region of cDNA. Further, a primer was produced upstream of clone 7-1 in order to confirm whether methionine present in clone 7-1 obtained in 6 above was an origin of replication. By this PCR, a PCR product P1 was obtained from the caudate nucleus cDNA library. From these results, 10 cDNA clones and PCR products were obtained (FIG. 2D).

As a result of determination of the nucleotide sequences of these cDNA clones, a 6,220 bp cDNA sequence was obtained and designated TRPC7. The nucleotide sequence of TRPC7 cDNA and its deduced amino acid sequence are shown in SEQ ID NO:1. First methionine occurring at nt 446 did not follow the rule of Kozak [53], but there was a stop codon 81 bp upstream from methionine within the same reading frame, and thus this methionine was determined to be an initiation codon. The ORF of TRPC7 encoded 1,503 amino acids for a protein having an isoelectric point of 7.26 and a molecular weight of 171,217.

7. Gene Structure of TRPC7

Figure 2:
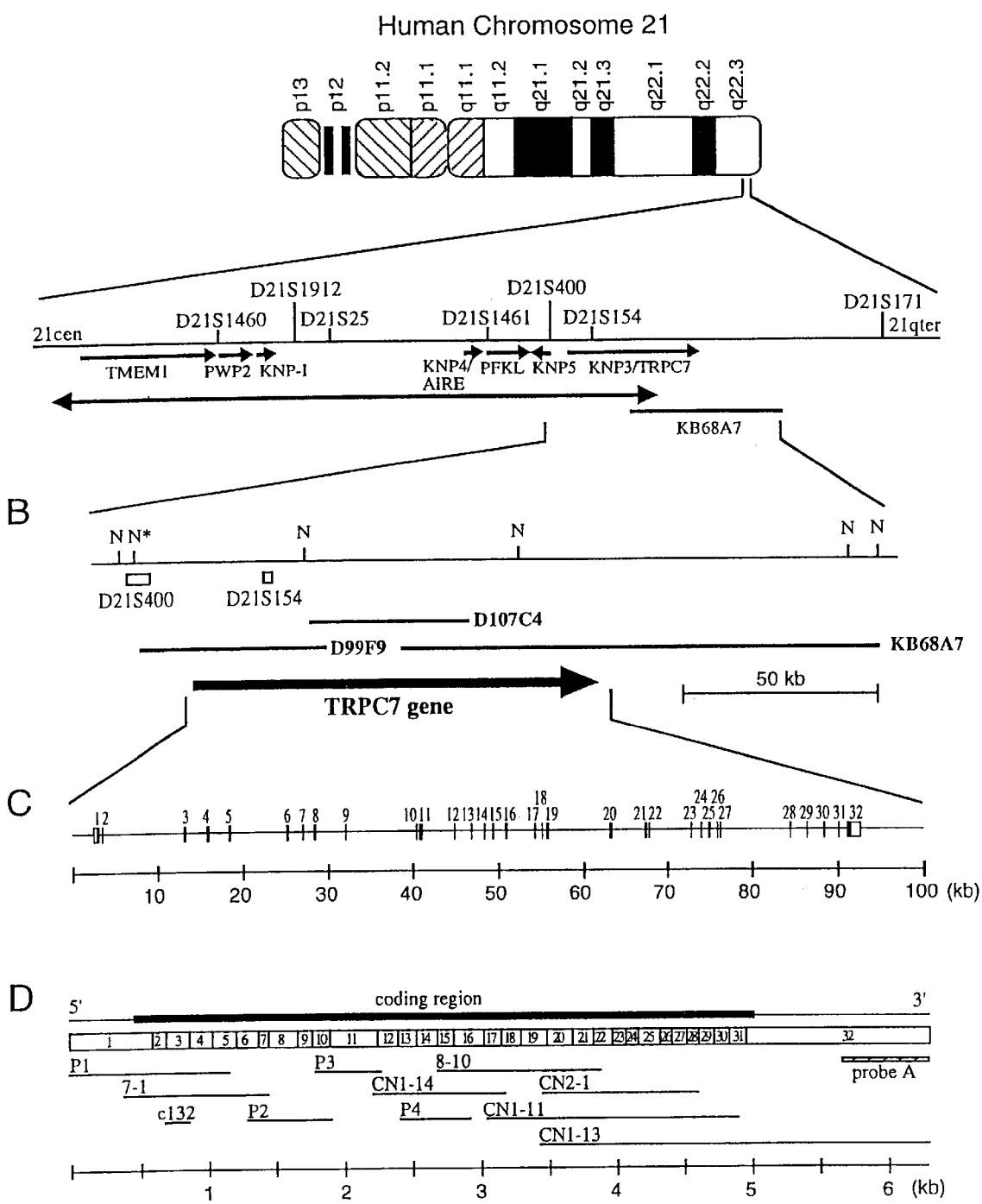
FIG. 2 shows the structure of a TRPC7 gene.

As a result of genome sequencing of 2 cosmids (D99F9, D107C4) and 1 BAC (KB68A7), the direction of transcription of TRPC7 was found to be from centromere to telomere (FIG. 2B). The exon intron structure is shown in Table 2. A common splice site ag:gt was conserved in each intron. These results indicated that the TRPC7 gene consisted of 32 exons, and its size was 95-kb (FIG. 2C).

TABLE 2

Exon-Intron Boundaries of the TRPC7 Gene

| exon | size(bp) | 3' acceptor site | 5' donor site |
|---|---|---|---|
| 1 | >610 |  | CAATGACAAGgtaggctttc |
| 2 | 89 | ttaccttcagCAAGAAAGCC | CTGATGCTGGgtaagtgacg |
| 3 | 169 | gtctttgcagGAAGGTGGTG | GGTGAAAAAGgttggtttcc |
| 4 | 181 | tttcccgcagTACGTCCGAG | CAGACCACAGgtaactcgga |
| 5 | 167 | ccttccccagGGGCCTGGAT | CCATCCCACGgtgagtgcgg |
| 6 | 181 | gccatcccagGGCAGCTTCC | GAAAGAGGAGgtagggagc |
| 7 | 62 | cttttttctagGTGTGGCCAT | CACGTTGCACgtgagtatgg |
| 8 | 201 | tgccttgcagACCATCGACA | GACCAAAAAGgtgaggctga |
| 9 | 103 | cttgttgcagATCCAAGATA | TTGCTGAAAGgtgagggtca |
| 10 | 122 | tcatctgcagCCTCACGGAG | GCAGTGGAAGgtaagtcttc |
| 11 | 354 | ttgctctcagCCTTCAGATC | CAAGCTCAACgtgcgtgctg |
| 12 | 138 | tgctcaccagGTGCAGGGAG | CTGGGCTCAGgtaataagac |
| 13 | 130 | cggtcccagAGCCAGGACT | AGAGCCATCGgtgagctctg |
| 14 | 146 | ctccgcccagGGGTCTTCAC | GGGCATCCAGgtgacctccc |
| 15 | 113 | ccatccgcagGCCTTCCTGA | TCTCCTTCAGgtgctgcagg |
| 16 | 217 | acggccgcagGGAGAAGAGG | GATGCGGCAGgtacagcccc |
| 17 | 119 | ttcccagtagCTCTTCTATG | TGACCTGCAGgtgagtggcc |
| 18 | 133 | cggcggccagGCTCATCCCG | GAAGCGGATGgtaaggggc |
| 19 | 172 | tgtcctgcagATGAAGGACG | TACATCGACGgtaggagccg |
| 20 | 184 | ccaacgccagGTGTGAACTT | CCATGTTCAAgtgagcgcct |
| 21 | 182 | tccctgacagCTACACCTTC | AAGCAGCTCAgtatgccagc |
| 22 | 133 | accctgacagAGAACAAGCT | TCAGCAATAAgtatggggc |
| 23 | 88 | cctctttcagGGTTGACGCC | GGAGGAGCAGgtgggtccga |
| 24 | 88 | tgccttccagGTGGCCCAGA | CCCACTCTGGgtgagtgggt |
| 25 | 158 | ctgtccccagCCTCCCAGAA | GCCCTGGGAGgtgagcgcct |
| 26 | 77 | tttgcgacagACGGAGTTCC | CCATGGGAGAgtgagtatga |
| 27 | 102 | ctgctcccagCACCCTGGAG | GGTTGCCCCTgtgagtgtgc |
| 28 | 87 | tgcatcccagGAACCCCATG | TGGTCACGCGgtgagttcat |
| 29 | 106 | ctctccgcagGTGGAGGCGG | CCTGCCTGGGgtaaggctgc |
| 30 | 102 | gtctgtccagGGCTCCCGGG | CGGCATGGAGgtattcctgg |
| 31 | 117 | gcccatccagGTGTACAAAG | GCTGAACTCTgtatgtgcct |
| 32 | >1389 | gttcttccagAACCTGCACG |  |

8. Analysis of Transmembrane Regions

Seven transmembrane sites were predicted with a program for predicting a transmembrane region from an amino acid sequence (FIG. 3). As a result of searching for homology in a protein database, it showed homology with Ca2+ channel proteins i.e. Drosophila TRP protein and human TRP protein [54][55][56][57]. FIG. 3 showed comparison between the transmembrane regions 2 to 7 and transmembrane regions in Drosophila TRP protein and human TRP protein. The respective domains of TRPC7 resembled those of human TRP proteins (Htrp-1, Htrp-2), and domains 2, 3, 4, 5, 6, and 7 had 8.3%, 24.0%, 12.0 %, 16.0%, 12.5% and 20.0% homology therewith, respectively. Further, when similar amino acids were incorporated, their homology was 20.8%, 40.0%, 36.0%, 32.0%, 41.7% and 52.0%, respectively. In human TRP protein, there was no sequence corresponding to domain 1 in TRPC7.

It is known that 6 transmembrane domains S1 to S6 are present in Drosophila TRP protein. The distribution of the 6 transmembrane domains in Drosophila TRP proteins (Dtrp, Dtrpl) mached well with those of TRPC7 protein. From the foregoing, it was suggested that the transmembrane regions in TRPC7, similar to those of other TRP proteins, functions as Ca2+ channel.

9. Northern Blot Analysis

Figure 4:
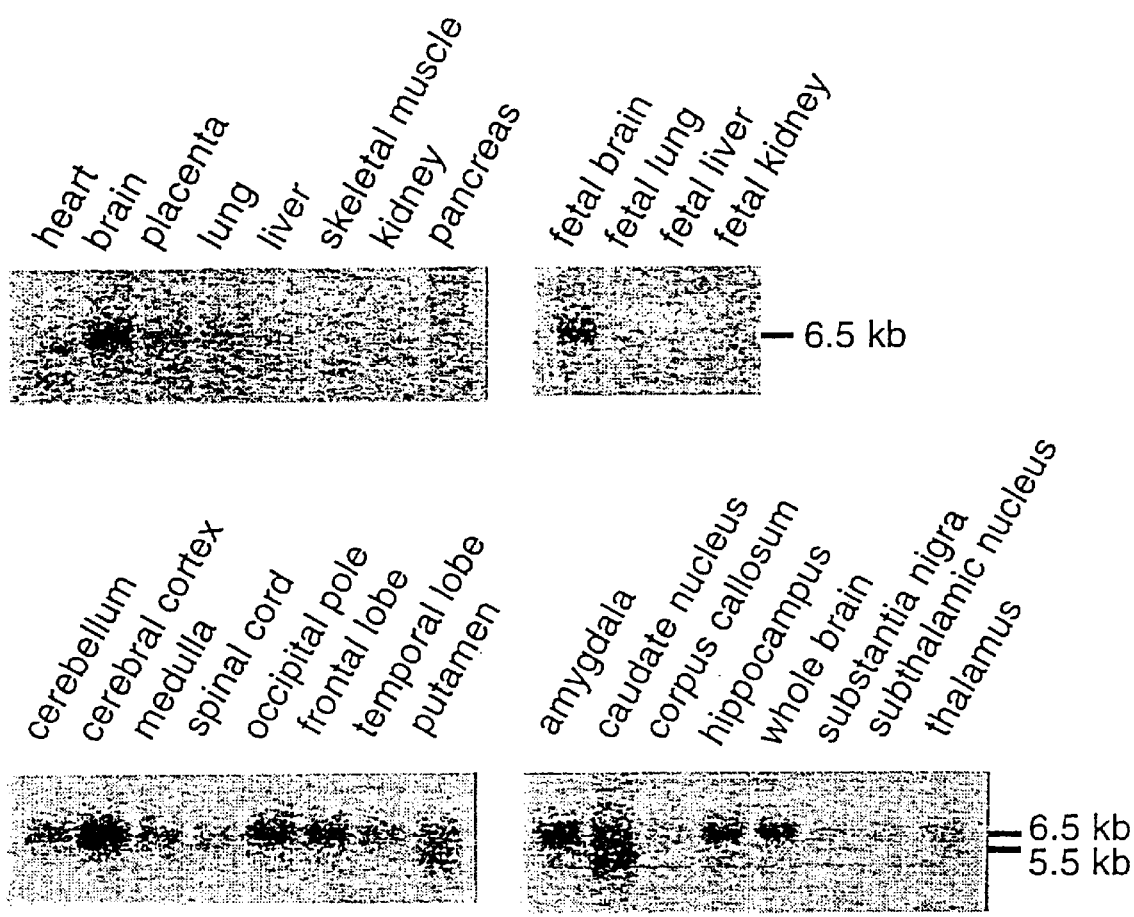
FIG. 4 shows Northern blot analysis of expression of the TRPC7 gene in various human tissues.

The organ-specificity of, expression of the TRPC7 gene was examined by Northern blot techniques. The probe (probe A) was amplified by PCR from cDNA clone CN1-13 by use of TRPC7. 5267 primer (5'-ACGAGGCTGCAGAAGCTCT-3') and λgt10 vector, primer (5'-CTTCCAGGGTAAAAAGCAAAAG-3'). An about 6.5-kb transcription product was observed in the fetal and adult brains and weakly observed in the placenta (FIG. 4, upper). In the brain, it was expressed in a relatively large amount in the cerebral cortex, occiput lobe pole, frontal lobe, cerebellar tonsils, caudate nucleus, and hippocampus (FIG. 4, below). In addition, 6.5-kb and 5.5-kb transcription products were observed in the caudate nucleus and putamen. Southern hybridization of entire human DNA previously digested with Eco RI, Hind III and BamH I or KB68A7 blot was carried out with probe A. As a result, the same hybridization pattern was observed, and it was suggested that probe A was the sequence of a single copy. That is, the 5.5-kb product was considered to be an alternative splicing product. Because the brain-specific expression pattern is shown, it can be estimated that TRPC7 plays an important role in functioning in the nerve system.

10. Genetic Analysis of Patients with Bipolar Affective Disorder

A mutation in the TRPC7 gene in patients with bipolar affective disorder was analyzed by PCR. Primers (containing sequences shown in Table 2) for amplification of all exon regions including exon 5 were prepared and these were used for PCR amplification of DNA prepared from lymphocytes in peripheral blood in patients with bipolar bipolar affective disorder. In 10 samples out of 20 samples from the patients, it was confirmed that there was a mutation in exon 5 in TRPC7. This mutation was not confirmed in control samples from healthy persons. It is thus considered that TRPC7 is a pathogenic gene for bipolar affective disorder.

INDUSTRIAL APPLICABILITY

According to the present invention, a pathogenic gene for bipolar affective disorder suspected heretofore of a genetic factor can be specified. By this, a significant advancement in the field of diagnosis and therapy of bipolar affective disorder can be expected. In the field of diagnosis, the clinical examination of bipolar affective disorder whose diagnosis was feasible by only clinical symptoms in the past could be established. One of examination methods is diagnosis of bipolar affective disorder by measuring TRPC7 in patient tissues. Further, genetic diagnosis of bipolar affective disorder becomes feasible by measuring a mutation in the TRPC7 gene. These diagnostic methods are useful for judgement of therapeutic effect or for monitoring therapeutic progress for treatment of bipolar affective disorder.

In addition, the present invention is useful for treatment of bipolar affective disorder. It is considered that the TRPC7 protein not only serves as a therapeutic agent for bipolar affective disorder but is also useful for in vitro screening a therapeutic agent for bipolar affective disorder and for judgement of the effect thereof. Furthermore, gene therapy for bipolar affective disorder is considered feasible by introducing a vector having the TRPC7 gene integrated therein into the body of a patient.

REFERENCES

[1] Seishin Igaku (Psychiatry), edited by Sadanori Miura, Nippon Ijishinposha
[2] Nature 325: 783–787(1987)
[3] Nature 326: 289–292(1987)
[4] Lancet i: 1230–1232(1987)
[5] Nature Genet. 12: 427–430(1996)
[6] Nature Genet. 12: 436–441(1996)
[7] Proc. Natl. Acad. Sci. USA 91: 5918–5921(1994)
[8] Nature Genet. 8: 291–296(1994)
[9] Nature Genet. 12: 431–435(1996)
[10] Brain Science 20: 253–257(1998)
[11] Proc. Natl. Acad. Sci. USA 86: 821–824(1989)
[12] Cell 37: 767(1984)
[13] WO94/03620
[14] WO96/04382
[15] Molecular Cloning: a laboratory manual, 2nd ed. (1989)
[16] Basic Methods in Molecular Biology, (1986)
[17] Cell 23: 175(1981)
[18] Nature 324: 163–166(1986)
[19] Science 230: 1242(1985)
[20] Proc. Natl. Acad. Sci. USA 85: 4397–4401(1985)
[21] Nature: 256: 495–497(1975)
[22] Immunology Today 4: 72(1983)
[23] Monoclonal Antibodies and Cancer Therapy, 77–96 (1985)
[24] U.S. Pat. No. 4,946,778
[25] Current Protocols in Immunology 1(2):(1991)
[26] U.S. Pat. No. 5,283,173
[27] Science 241: 585–589(1988)
[28] EMBO. J. 10: 2821-2831(1991)
[29] Proc. Natl. Acad. Sci. USA 84: 3365(1987)
[30] EMBO. J. 6: 3313(1987)
[31] Science 228: 810–815(1985)
[32] WO92/01810
[33] Science 246: 181–296(1989)
[34] U.S. Pat. No. 5,482,835
[35] Nucl. Acids Res. 6: 3073(1979)
[36] Science 241: 456(1988)
[37] Science 251: 1360(1991)
[38] J. Neurochem. 56: 560(1991)
[39] Oligodeoxynucleotides as Antisense Inhibitors of Gene Expression, (1988)
[40] Biotechniques 7: 980–990(1989)
[41] Human Gene Therapy 1: 5–14(1990)
[42] Nucleic Acids Res. 8: 4057(1980)
[43] Cytometry 11: 539–546(1990)

[44] Gene 79: 9–20(1989)
[45] DNA reseach 4: 45–52(1997)
[46] Genomics 29: 288–290(1995)
[47] Gene 191: 69–79(1997)
[48] Proc. Natl. Acad. Sci. USA 85: 2444–2448(1988)
[49] J. Mol. Biol. 215: 403–410(1990)
[50] Genomics 7: 47–56(1990)
[51] Genet. 4: 709–716(1995)
[52] Proc. Natl. Acad. Sci. USA. 88: 11261–11265(1991)
[53] Nucl. Acids Res. 12: 857–872(1984)
[54] Neuron 2: 1313–1323(1989)
[55] Neuron 8: 631–642(1992)
[56] Cell 85: 661–671(1996)
[57] Neuron 16: 1189–1196(1996)

What is claimed is:

1. An isolated polynucleotide comprising a polynucleotide selected from the group consisting of:

(a) a polynucleotide coding for a polypeptide consisting of amino acids shown in SEQ ID NO:2;

(b) a polynucleotide resulting from degeneracy of genetic code coding for the same amino acids as in SEQ ID NO:2;

(c) a polynucleotide complementary to the polynucleotide of (a) or (b); and (d) a polynucleotide consisting of at least 15 contiguous nucleotides from the polynucleotide of (a), (b), or (c).

2. The polynucleotide according to claim 1, wherein the polynucleotide is DNA.

3. The polynucleotide according to claim 1, wherein the polynucleotide is RNA.

4. The polynucleotide according to claim 2, which comprises the nucleotide sequence shown in SEQ ID NO:1.

5. The polynucleotide according to claim 2, which comprises the nucleotide sequence at 1- to 6220-positions in SEQ ID NO:1.

6. The polynucleotide according to claim 2, which codes for a polypeptide comprising the amino acids in SEQ ID NO:2.

7. A vector comprising the DNA described in claim 2.

8. An isolated host cell comprising the vector described in claim 7.

9. A method of producing a polypeptide, which comprises allowing the host described in claim 8 to express a polypeptide encoded by said DNA.

10. A method of producing cells expressing a polypeptide, which comprises transforming or transfecting cells with the vector described in claim 7 so as to permit the cells to express a polypeptide encoded by the DNA contained in said vector.

11. An isolated polypeptide comprising the amino acid sequence shown in SEQ ID NO:2.

* * * * *

SEQUENCE LISTING

<160> NUMBER OF SEQ ID NOS: 2

<210> SEQ ID NO 1
<211> LENGTH: 6220
<212> TYPE: DNA
<213> ORGANISM: Homo sapiens
<220> FEATURE:
<221> NAME/KEY: CDS
<222> LOCATION: (446)...(4954)
<221> NAME/KEY: polyA_signal
<222> LOCATION: (5812)...(5817)

<400> SEQUENCE: 1

```
tgtgcagaat tgtacagttg cgaaaccatg tcgctggcag ctggtgctgg cggtggagac      60
ttccctgtgc ggtgctcagt gcatctgcac ccgtggggga gggagctctt tctctggccc     120
tgcagtcacc tgaggttgtt accattatga acggccgctg ggaccccgc atgtgcatgt      180 actcccccag agtgtccggg ggccccagcc aagggacaca tctcacgcag ctgggaacat     240
gtgcaggctg atgaagagaa ccggatgagg gcttcacatg aggaagcatg tggccaggtc     300
ctctcagaac atcagcctca tcttcctgtc tctgatctat ttcaccaacc accccatgtg     360
tctctagaac cccagtgtag cgagctggag agaggactgt cctgagggca gcaggcctgg     420
ttgcagctgg cgtgggggtc tcaga atg gag ccc tca gcc ctg agg aaa gct      472
                              Met Glu Pro Ser Ala Leu Arg Lys Ala
                                1               5 ggc tcg gag cag gag gag ggc ttt gag ggg ctg ccc aga agg gtc act      520
Gly Ser Glu Gln Glu Glu Gly Phe Glu Gly Leu Pro Arg Arg Val Thr
 10              15                  20                  25 gac ctg ggg atg gtc tcc aat ctc cgg cgc agc aac agc agc ctc ttc      568
Asp Leu Gly Met Val Ser Asn Leu Arg Arg Ser Asn Ser Ser Leu Phe
                 30                  35                  40 aag agc tgg agg cta cag tgc ccc ttc ggc aac aat gac aag caa gaa      616
Lys Ser Trp Arg Leu Gln Cys Pro Phe Gly Asn Asn Asp Lys Gln Glu
             45                  50                  55 agc ctc agt tcg tgg att cct gaa aac atc aag aag aaa gaa tgc gtg      664
Ser Leu Ser Ser Trp Ile Pro Glu Asn Ile Lys Lys Lys Glu Cys Val
         60                  65                  70 tat ttt gtg gaa agt tcc aaa ctg tct gat gct ggg aag gtg gtg tgt      712
Tyr Phe Val Glu Ser Ser Lys Leu Ser Asp Ala Gly Lys Val Val Cys
     75                  80                  85 cag tgt ggc tac acg cat gag cag cac ttg gag gag gct acc aag ccc      760
Gln Cys Gly Tyr Thr His Glu Gln His Leu Glu Glu Ala Thr Lys Pro
 90                  95                 100                 105 cac acc ttc cag ggc aca cag tgg gac cca aag aaa cat gtc cag gag      808
His Thr Phe Gln Gly Thr Gln Trp Asp Pro Lys Lys His Val Gln Glu
                110                 115                 120 atg cca acc gat gcc ttt ggc gac atc gtc ttc acg ggc ctg agc cag      856
Met Pro Thr Asp Ala Phe Gly Asp Ile Val Phe Thr Gly Leu Ser Gln
                125                 130                 135 aag gtg aaa aag tac gtc cga gtc tcc cag gac acg ccc tcc agc gtg      904
Lys Val Lys Lys Tyr Val Arg Val Ser Gln Asp Thr Pro Ser Ser Val
```

```
              140                 145                 150
atc tac cac ctc atg acc cag cac tgg ggg ctg gac gtc ccc aat ctc    952
Ile Tyr His Leu Met Thr Gln His Trp Gly Leu Asp Val Pro Asn Leu
    155                 160                 165 ttg atc tcg gtg acc ggg ggg gcc aag aac ttc aac atg aag ccg cgg   1000
Leu Ile Ser Val Thr Gly Gly Ala Lys Asn Phe Asn Met Lys Pro Arg
170                 175                 180                 185 ctg aag agc att ttc cgc aga ggc ctg gtc aag gtg gct cag acc aca   1048
Leu Lys Ser Ile Phe Arg Arg Gly Leu Val Lys Val Ala Gln Thr Thr
                190                 195                 200 ggg gcc tgg atc atc aca ggg ggg tcc cac acc ggc gtc atg aag cag   1096
Gly Ala Trp Ile Ile Thr Gly Gly Ser His Thr Gly Val Met Lys Gln
            205                 210                 215 gta ggc gag gcg gtg cgg gac ttc agc ctg agc agc agc tac aag gaa   1144
Val Gly Glu Ala Val Arg Asp Phe Ser Leu Ser Ser Ser Tyr Lys Glu
        220                 225                 230 ggc gag ctc atc acc atc gga gtc gcc acc tgg ggc act gtc cac cgc   1192
Gly Glu Leu Ile Thr Ile Gly Val Ala Thr Trp Gly Thr Val His Arg
    235                 240                 245 cgc gag ggc ctg atc cat ccc acg ggc agc ttc ccc gcc gag tac ata   1240
Arg Glu Gly Leu Ile His Pro Thr Gly Ser Phe Pro Ala Glu Tyr Ile
250                 255                 260                 265 ctg gat gag gat ggc caa ggg aac ctg acc tgc cta gac agc aac cac   1288
Leu Asp Glu Asp Gly Gln Gly Asn Leu Thr Cys Leu Asp Ser Asn His
                270                 275                 280 tct cac ttc atc ctc gtg gac gac ggg acc cac ggc cag tac ggg gtg   1336
Ser His Phe Ile Leu Val Asp Asp Gly Thr His Gly Gln Tyr Gly Val
            285                 290                 295 gag att cct ctg agg acc agg ctg gag aag ttc ata tcg gag cag acc   1384
Glu Ile Pro Leu Arg Thr Arg Leu Glu Lys Phe Ile Ser Glu Gln Thr
        300                 305                 310 aag gaa aga gga ggt gtg gcc atc aag atc ccc atc gtg tgc gtg gtg   1432
Lys Glu Arg Gly Gly Val Ala Ile Lys Ile Pro Ile Val Cys Val Val
    315                 320                 325 ctg gag ggc ggc ccg ggc acg ttg cac acc atc gac aac gcc acc acc   1480
Leu Glu Gly Gly Pro Gly Thr Leu His Thr Ile Asp Asn Ala Thr Thr
330                 335                 340                 345 aac ggc acc ccc tgt gtg gtt gtg gag ggc tcg ggc cgc gtg gcc gac   1528
Asn Gly Thr Pro Cys Val Val Val Glu Gly Ser Gly Arg Val Ala Asp
                350                 355                 360 gtc att gcc cag gtg gcc aac ctg cct gtc tcg gac atc act atc tcc   1576
Val Ile Ala Gln Val Ala Asn Leu Pro Val Ser Asp Ile Thr Ile Ser
            365                 370                 375 ctg atc cag cag aaa ctg agc gtg ttc ttc cag gag atg ttt gag acc   1624
Leu Ile Gln Gln Lys Leu Ser Val Phe Phe Gln Glu Met Phe Glu Thr
        380                 385                 390 ttc acg gaa agc agg att gtc gag tgg acc aaa aag atc caa gat att   1672
Phe Thr Glu Ser Arg Ile Val Glu Trp Thr Lys Lys Ile Gln Asp Ile
    395                 400                 405 gtc cgg agg cgg cag ctg ctg act gtc ttc cgg gaa ggc aag gat ggt   1720
Val Arg Arg Arg Gln Leu Leu Thr Val Phe Arg Glu Gly Lys Asp Gly
410                 415                 420                 425 cag cag gac gtg gat gtg gcc atc ttg cag gcc ttg ctg aaa gcc tca   1768
Gln Gln Asp Val Asp Val Ala Ile Leu Gln Ala Leu Leu Lys Ala Ser
                430                 435                 440 cgg agc caa gac cac ttt ggc cac gag aac tgg gac cac cag ctg aaa   1816
Arg Ser Gln Asp His Phe Gly His Glu Asn Trp Asp His Gln Leu Lys
            445                 450                 455 ctg gca gtg gca tgg aat cgc gtg gac att gcc cgc agt gag atc ttc   1864
```

```
                                                                    -continued Leu Ala Val Ala Trp Asn Arg Val Asp Ile Ala Arg Ser Glu Ile Phe
            460                 465                 470 atg gat gag tgg cag tgg aag cct tca gat ctg cac ccc acg atg aca        1912
Met Asp Glu Trp Gln Trp Lys Pro Ser Asp Leu His Pro Thr Met Thr
475                 480                 485 gct gca ctc atc tcc aac aag cct gag ttt gtg aag ctc ttc ctg gaa        1960
Ala Ala Leu Ile Ser Asn Lys Pro Glu Phe Val Lys Leu Phe Leu Glu
490                 495                 500                 505 aac ggg gtg cag ctg aag gag ttt gtc acc tgg gac acc ttg ctc tac        2008
Asn Gly Val Gln Leu Lys Glu Phe Val Thr Trp Asp Thr Leu Leu Tyr
                510                 515                 520 ctg tac gag aac ctg gac ccc tcc tgc ctg ttc cac agc aag ctg caa        2056
Leu Tyr Glu Asn Leu Asp Pro Ser Cys Leu Phe His Ser Lys Leu Gln
            525                 530                 535 aag gtg ctg gtg gag gat ccc gag cgc ccg gct tgc gcg ccc gcg gcg        2104
Lys Val Leu Val Glu Asp Pro Glu Arg Pro Ala Cys Ala Pro Ala Ala
        540                 545                 550 ccc cgc ctg cag atg cac cac gtg gcc cag gtg ctg cgg gag ctg ctg        2152
Pro Arg Leu Gln Met His His Val Ala Gln Val Leu Arg Glu Leu Leu
    555                 560                 565 ggg gac ttc acg cag ccg ctt tat ccc cgg ccc cgg cac aac gac cgg        2200
Gly Asp Phe Thr Gln Pro Leu Tyr Pro Arg Pro Arg His Asn Asp Arg
570                 575                 580                 585 ctg cgg ctc ctg ctg ccc gtt ccc cac gtc aag ctc aac gtg cag gga        2248
Leu Arg Leu Leu Leu Pro Val Pro His Val Lys Leu Asn Val Gln Gly
                590                 595                 600 gtg agc ctc cgg tcc ctc tac aag cgt tcc tca ggc cat gtg acc ttc        2296
Val Ser Leu Arg Ser Leu Tyr Lys Arg Ser Ser Gly His Val Thr Phe
            605                 610                 615 acc atg gac ccc atc cgt gac ctt ctc att tgg gcc att gtc cag aac        2344
Thr Met Asp Pro Ile Arg Asp Leu Leu Ile Trp Ala Ile Val Gln Asn
        620                 625                 630 cgt cgg gag ctg gca gga atc atc tgg gct cag agc cag gac tgc atc        2392
Arg Arg Glu Leu Ala Gly Ile Ile Trp Ala Gln Ser Gln Asp Cys Ile
    635                 640                 645 gca gcg gcc ttg gcc tgc agc aag atc ctg aag gaa ctg tcc aag gag        2440
Ala Ala Ala Leu Ala Cys Ser Lys Ile Leu Lys Glu Leu Ser Lys Glu
650                 655                 660                 665 gag gag gac acg gac agc tcg gag gag atg ctg gcg ctg gcg gag gag        2488
Glu Glu Asp Thr Asp Ser Ser Glu Glu Met Leu Ala Leu Ala Glu Glu
                670                 675                 680 tat gag cac aga gcc atc ggg gtc ttc acc gag tgc tac cgg aag gac        2536
Tyr Glu His Arg Ala Ile Gly Val Phe Thr Glu Cys Tyr Arg Lys Asp
            685                 690                 695 gaa gag aga gcc cag aaa ctg ctc acc cgc gtg tcc gag gcc tgg ggg        2584
Glu Glu Arg Ala Gln Lys Leu Leu Thr Arg Val Ser Glu Ala Trp Gly
        700                 705                 710 aag acc acc tgc ctg cag ctc gcc ctg gag gcc aag gac atg aag ttt        2632
Lys Thr Thr Cys Leu Gln Leu Ala Leu Glu Ala Lys Asp Met Lys Phe
715                 720                 725 gtg tct cac ggg ggc atc cag gcc ttc ctg acc aag gtg tgg tgg ggc        2680
Val Ser His Gly Gly Ile Gln Ala Phe Leu Thr Lys Val Trp Trp Gly
730                 735                 740                 745 cag ctc tcc gtg gac aat ggg ctg tgg cgt gtg acc ctg tgc atg ctg        2728
Gln Leu Ser Val Asp Asn Gly Leu Trp Arg Val Thr Leu Cys Met Leu
                750                 755                 760 gcc ttc ccg ctg ctc ctc acc ggc ctc atc tcc ttc agg gag aag agg        2776
Ala Phe Pro Leu Leu Leu Thr Gly Leu Ile Ser Phe Arg Glu Lys Arg
            765                 770                 775
```

```
ctg cag gat gtg ggc acc ccc gcg gcc cgc gcc cgt gcc ttc ttc acc    2824
Leu Gln Asp Val Gly Thr Pro Ala Ala Arg Ala Arg Ala Phe Phe Thr
        780                 785                 790 gca ccc gtg gtg gtc ttc cac ctg aac atc ctc tcc tac ttc gcc ttc    2872
Ala Pro Val Val Val Phe His Leu Asn Ile Leu Ser Tyr Phe Ala Phe
    795                 800                 805 ctc tgc ctg ttc gcc tac gtg ctc atg gtg gac ttc cag cct gtg ccc    2920
Leu Cys Leu Phe Ala Tyr Val Leu Met Val Asp Phe Gln Pro Val Pro
810                 815                 820                 825 tcc tgg tgc gag tgt gcc atc tac ctc tgg ctc ttc tcc ttg gtg tgc    2968
Ser Trp Cys Glu Cys Ala Ile Tyr Leu Trp Leu Phe Ser Leu Val Cys
                830                 835                 840 gag gag atg cgg cag ctc ttc tat gac cct gac gag tgc ggg ctg atg    3016
Glu Glu Met Arg Gln Leu Phe Tyr Asp Pro Asp Glu Cys Gly Leu Met
            845                 850                 855 aag aag gca gcc ttg tac ttc agt gac ttc tgg aat aag ctg gac gtc    3064
Lys Lys Ala Ala Leu Tyr Phe Ser Asp Phe Trp Asn Lys Leu Asp Val
        860                 865                 870 ggc gca atc ttg ctc ttc gtg gca ggg ctg acc tgc agg ctc atc ccg    3112
Gly Ala Ile Leu Leu Phe Val Ala Gly Leu Thr Cys Arg Leu Ile Pro
    875                 880                 885 gcg acg ctg tac ccc ggg cgc gtc atc ctc tct ctg gac ttc atc ctg    3160
Ala Thr Leu Tyr Pro Gly Arg Val Ile Leu Ser Leu Asp Phe Ile Leu
890                 895                 900                 905 ttc tgc ctc cgg ctc atg cac att ttt acc atc agt aag acg ctg ggg    3208
Phe Cys Leu Arg Leu Met His Ile Phe Thr Ile Ser Lys Thr Leu Gly
                910                 915                 920 ccc aag atc atc att gtg aag cgg atg atg aag gac gtc ttc ttc ttc    3256
Pro Lys Ile Ile Ile Val Lys Arg Met Met Lys Asp Val Phe Phe Phe
            925                 930                 935 ctc ttc ctg ctg gct gtg tgg gtg gtg tcc ttc ggg gtg gcc aag cag    3304
Leu Phe Leu Leu Ala Val Trp Val Val Ser Phe Gly Val Ala Lys Gln
        940                 945                 950 gcc atc ctc atc cac aac gag cgc cgg gtg gac tgg ctg ttc cga ggg    3352
Ala Ile Leu Ile His Asn Glu Arg Arg Val Asp Trp Leu Phe Arg Gly
    955                 960                 965 gcc gtc tac cac tcc tac ctc acc atc ttc ggg cag atc ccg ggc tac    3400
Ala Val Tyr His Ser Tyr Leu Thr Ile Phe Gly Gln Ile Pro Gly Tyr
970                 975                 980                 985 atc gac ggt gtg aac ttc aac ccg gag cac tgc agc ccc aat ggc acc    3448
Ile Asp Gly Val Asn Phe Asn Pro Glu His Cys Ser Pro Asn Gly Thr
                990                 995                 1000 gac ccc tac aag cct aag tgc ccc gag agc gac gcg acg cag cag agg    3496
Asp Pro Tyr Lys Pro Lys Cys Pro Glu Ser Asp Ala Thr Gln Gln Arg
            1005                1010                1015 ccg gcc ttc cct gag tgg ctg acg gtc ctc cta ctc tgc ctc tac ctg    3544
Pro Ala Phe Pro Glu Trp Leu Thr Val Leu Leu Leu Cys Leu Tyr Leu
        1020                1025                1030 ctc ttc acc aac atc ctg ctg ctc aac ctc ctc atc gcc atg ttc aac    3592
Leu Phe Thr Asn Ile Leu Leu Leu Asn Leu Leu Ile Ala Met Phe Asn
    1035                1040                1045 tac acc ttc cag cag gtg cag gag cac acg gac cag att tgg aag ttc    3640
Tyr Thr Phe Gln Gln Val Gln Glu His Thr Asp Gln Ile Trp Lys Phe
1050                1055                1060                1065 cag cgc cat gac ctg atc gag gag tac cac ggc cgc ccc gcc gcg ccg    3688
Gln Arg His Asp Leu Ile Glu Glu Tyr His Gly Arg Pro Ala Ala Pro
                1070                1075                1080 ccc ccc ttc atc ctc ctc agc cac ctg cag ctc ttc atc aag agg gtg    3736
Pro Pro Phe Ile Leu Leu Ser His Leu Gln Leu Phe Ile Lys Arg Val
            1085                1090                1095
```

-continued

```
gtc ctg aag act ccg gcc aag agg cac aag cag ctc aag aac aag ctg      3784
Val Leu Lys Thr Pro Ala Lys Arg His Lys Gln Leu Lys Asn Lys Leu
        1100                1105                1110 gag aag aac gag gag gcg gcc ctg cta tcc tgg gag atc tac ctg aag      3832
Glu Lys Asn Glu Glu Ala Ala Leu Leu Ser Trp Glu Ile Tyr Leu Lys
1115                1120                1125 gag aac tac ctc cag aac cga cag ttc cag caa aag cag cgg ccc gag      3880
Glu Asn Tyr Leu Gln Asn Arg Gln Phe Gln Gln Lys Gln Arg Pro Glu
1130                1135                1140                1145 cag aag atc gag gac atc agc aat aag gtt gac gcc atg gtg gac ctg      3928
Gln Lys Ile Glu Asp Ile Ser Asn Lys Val Asp Ala Met Val Asp Leu
            1150                1155                1160 ctg gac ctg gac cca ctg aag agg tcg ggc tcc atg gag cag agg ttg      3976
Leu Asp Leu Asp Pro Leu Lys Arg Ser Gly Ser Met Glu Gln Arg Leu
        1165                1170                1175 gcc tcc ctg gag gag cag gtg gcc cag aca gcc cga gcc ctg cac tgg      4024
Ala Ser Leu Glu Glu Gln Val Ala Gln Thr Ala Arg Ala Leu His Trp
    1180                1185                1190 atc gtg agg acg ctg cgg gcc agc ggc ttc agc tcg gag gcg gac gtc      4072
Ile Val Arg Thr Leu Arg Ala Ser Gly Phe Ser Ser Glu Ala Asp Val
    1195                1200                1205 ccc act ctg gcc tcc cag aag gcc gcg gag gag ccg gat gct gag ccg      4120
Pro Thr Leu Ala Ser Gln Lys Ala Ala Glu Glu Pro Asp Ala Glu Pro
1210                1215                1220                1225 gga ggc agg aag aag acg gag gag ccg ggc gac agc tac cac gtg aat      4168
Gly Gly Arg Lys Lys Thr Glu Glu Pro Gly Asp Ser Tyr His Val Asn
            1230                1235                1240 gcc cgg cac ctc ctc tac ccc aac tgc cct gtc acg cgc ttc ccc gtg      4216
Ala Arg His Leu Leu Tyr Pro Asn Cys Pro Val Thr Arg Phe Pro Val
        1245                1250                1255 ccc aac gag aag gtg ccc tgg gag acg gag ttc ctg atc tat gac cca      4264
Pro Asn Glu Lys Val Pro Trp Glu Thr Glu Phe Leu Ile Tyr Asp Pro
    1260                1265                1270 ccc ttt tac acg gca gag agg aag gac gcg gcc gcc atg gac ccc atg      4312
Pro Phe Tyr Thr Ala Glu Arg Lys Asp Ala Ala Ala Met Asp Pro Met
    1275                1280                1285 gga gac acc ctg gag cca ctg tcc acg atc cag tac aac gtg gtg gat      4360
Gly Asp Thr Leu Glu Pro Leu Ser Thr Ile Gln Tyr Asn Val Val Asp
1290                1295                1300                1305 ggc ctg agg gac cgc cgg agc ttc cac ggg ccg tac aca gtg cag gcc      4408
Gly Leu Arg Asp Arg Arg Ser Phe His Gly Pro Tyr Thr Val Gln Ala
            1310                1315                1320 ggg ttg ccc ctg aac ccc atg ggc cgc aca gga ctg cgt ggg cgc ggg      4456
Gly Leu Pro Leu Asn Pro Met Gly Arg Thr Gly Leu Arg Gly Arg Gly
        1325                1330                1335 agc ctc agc tgc ttc gga ccc aac cac acg ctg tac ccc atg gtc acg      4504
Ser Leu Ser Cys Phe Gly Pro Asn His Thr Leu Tyr Pro Met Val Thr
    1340                1345                1350 cgg tgg agg cgg aac gag gat gga gcc atc tgc agg aag agc ata aag      4552
Arg Trp Arg Arg Asn Glu Asp Gly Ala Ile Cys Arg Lys Ser Ile Lys
    1355                1360                1365 aag atg ctg gaa gtg ctg gtg gtg aag ctc cct ctc tcc gag cac tgg      4600
Lys Met Leu Glu Val Leu Val Val Lys Leu Pro Leu Ser Glu His Trp
1370                1375                1380                1385 gcc ctg cct ggg ggc tcc cgg gag cca ggg gag atg cta cct cgg aag      4648
Ala Leu Pro Gly Gly Ser Arg Glu Pro Gly Glu Met Leu Pro Arg Lys
            1390                1395                1400 ctg aag cgg atc ctc cgg cag gag cac tgg ccg tct ttt gaa aac ttg      4696
Leu Lys Arg Ile Leu Arg Gln Glu His Trp Pro Ser Phe Glu Asn Leu
```

|  |  |  |  |  |  |  |  |  |  |  |  |  |  |  |  |
|---|---|---|---|---|---|---|---|---|---|---|---|---|---|---|---|
| | | | | 1405 | | | | | 1410 | | | | | 1415 | |
| ctg | aag | tgc | ggc | atg | gag | gtg | tac | aaa | ggc | tac | atg | gat | gac | ccg | agg |
| Leu | Lys | Cys | Gly | Met | Glu | Val | Tyr | Lys | Gly | Tyr | Met | Asp | Asp | Pro | Arg |
| | | | | 1420 | | | | | 1425 | | | | | 1430 | |

4744 aac acg gac aat gcc tgg atc gag acg gtg gcc gtc agc gtc cac ttc    4792
Asn Thr Asp Asn Ala Trp Ile Glu Thr Val Ala Val Ser Val His Phe
    1435                1440                1445 cag gac cag aat gac gtg gag ctg aac agg ctg aac tct aac ctg cac    4840
Gln Asp Gln Asn Asp Val Glu Leu Asn Arg Leu Asn Ser Asn Leu His
1450                1455                1460                1465 gcc tgc gac tcg ggg gcc tcc atc cga tgg cag gtg gtg gac agg cgc    4888
Ala Cys Asp Ser Gly Ala Ser Ile Arg Trp Gln Val Val Asp Arg Arg
                1470                1475                1480 atc cca ctc tat gcg aac cac aag acc ctc ctc cag aag gca gcc gct    4936
Ile Pro Leu Tyr Ala Asn His Lys Thr Leu Leu Gln Lys Ala Ala Ala
            1485                1490                1495 gag ttc ggg gct cac tac tgactgtgcc ctcaggctgg gcggctccag            4984
Glu Phe Gly Ala His Tyr
        1500 tccatagacg ttcccccag aaaccagggc ttctctctcc tgagcctggc caggactcag   5044 gctgttcctg ggccctgcac atgatggggt ttggtggacc cagtgcccct cacggctgcc   5104 gcaagtctgc tgcagatgac ctcatgaact ggaaggggtc aagtgaccc gggaggagag   5164 ctcaagacag gcacaggct actcagagct gaggggcccc tgggacccett ggccatcagg   5224 cgaggggctg ggcctgtgca gctgggccct tggccagagt ccactccctt cctggctgtg   5284 tcaccccgag cagctcatcc accatggagg tcattggcct gaggcaagtt ccccggagag   5344 tcgggatccc ctgtggcccc ctcaggccta tgtctgtgag gaaggggccc tgccactctc   5404 cccaagaggg cctccatgtt tcgaggtgcc tcaacatgga gccttgcctg gcctgggcta   5464 ggggcactgt ctgaactcct gactgtcagg ataaactccg tggggtaca ggagcccaga   5524 caaagcccag gcctgtcaag agacgcagag ggcccctgcc agggttggcc ccagggaccc   5584 tgggacgagg ctgcagaagc tctccctccc tactccctgg gagccacgtg ctggccatgt   5644 ggccagggac ggcatgagca ggaggcgggg acgtgggggc cttctggttt ggtgtcaaca   5704 gctcacagga gcgtgaacca tgagggccct caggagggga acgtggtaaa acccaagaca   5764 ttaaatctgc catctcaggc ctggctggct cttctgtgct ttccacaaat aaagttcctg   5824 acacgtccag ggccaggggc tgtgtgacgg ctgcctgaag ttctcctcga tccccggtg   5884 agcttcctgc agcctgtgga tgtcctgcag ccctcagcc taccccaa gtttctcctc     5944 tgacccatca gctccctgtc ttcattttcc taaacctggg ctccagcatc gtccccaagc   6004 ccaccaggcc aggatgcagg catccacatg ccctcctcct tggcttcccc tgcgtggtgg   6064 tgccaatgtg ccctggcacc cctgcagagg ctccggatgg agcctggggc tgcctggcca   6124 ctgagcactg gccgaggtga tgcccaccct tccctggaca ggcctctgtc ttccacctga   6184 cccaaagctc tctagccacc cccttgtccc cagtat                            6220

<210> SEQ ID NO 2
<211> LENGTH: 1503
<212> TYPE: PRT
<213> ORGANISM: Homo sapiens
<220> FEATURE:
<221> NAME/KEY: TRANSMEM
<222> LOCATION: (320)...(344)
<221> NAME/KEY: TRANSMEM
<222> LOCATION: (750)...(773)
<221> NAME/KEY: TRANSMEM

```
<222> LOCATION: (794)...(818)
<221> NAME/KEY: TRANSMEM
<222> LOCATION: (867)...(891)
<221> NAME/KEY: TRANSMEM
<222> LOCATION: (900)...(924)
<221> NAME/KEY: TRANSMEM
<222> LOCATION: (932)...(956)
<221> NAME/KEY: TRANSMEM
<222> LOCATION: (1024)...(1048)

<400> SEQUENCE: 2
```

Met Glu Pro Ser Ala Leu Arg Lys Ala Gly Ser Glu Gln Glu Gly
 1               5                  10                  15

Phe Glu Gly Leu Pro Arg Arg Val Thr Asp Leu Gly Met Val Ser Asn
                 20                  25                  30

Leu Arg Arg Ser Asn Ser Ser Leu Phe Lys Ser Trp Arg Leu Gln Cys
             35                  40                  45

Pro Phe Gly Asn Asn Asp Lys Gln Glu Ser Leu Ser Ser Trp Ile Pro
     50                  55                  60

Glu Asn Ile Lys Lys Lys Glu Cys Val Tyr Phe Val Glu Ser Ser Lys
 65                  70                  75                  80

Leu Ser Asp Ala Gly Lys Val Val Cys Gln Cys Gly Tyr Thr His Glu
                 85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His Pro
                245                 250                 255

Thr Gly Ser Phe Pro Ala Glu Tyr Ile Leu Asp Glu Asp Gly Gln Gly
            260                 265                 270

Asn Leu Thr Cys Leu Asp Ser Asn His Ser His Phe Ile Leu Val Asp
        275                 280                 285

Asp Gly Thr His Gly Gln Tyr Gly Val Glu Ile Pro Leu Arg Thr Arg
    290                 295                 300

Leu Glu Lys Phe Ile Ser Glu Gln Thr Lys Glu Arg Gly Gly Val Ala
305                 310                 315                 320

Ile Lys Ile Pro Ile Val Cys Val Val Leu Glu Gly Gly Pro Gly Thr
                325                 330                 335

Leu His Thr Ile Asp Asn Ala Thr Thr Asn Gly Thr Pro Cys Val Val
            340                 345                 350

Val Glu Gly Ser Gly Arg Val Ala Asp Val Ile Ala Gln Val Ala Asn

-continued

```
                355                 360                 365
Leu Pro Val Ser Asp Ile Thr Ile Ser Leu Ile Gln Gln Lys Leu Ser
    370                 375                 380
Val Phe Phe Gln Glu Met Phe Glu Thr Phe Thr Glu Ser Arg Ile Val
385                 390                 395                 400
Glu Trp Thr Lys Lys Ile Gln Asp Ile Val Arg Arg Arg Gln Leu Leu
                405                 410                 415
Thr Val Phe Arg Glu Gly Lys Asp Gly Gln Gln Asp Val Asp Val Ala
                420                 425                 430
Ile Leu Gln Ala Leu Leu Lys Ala Ser Arg Ser Gln Asp His Phe Gly
                435                 440                 445
His Glu Asn Trp Asp His Gln Leu Lys Leu Ala Val Ala Trp Asn Arg
    450                 455                 460
Val Asp Ile Ala Arg Ser Glu Ile Phe Met Asp Glu Trp Gln Trp Lys
465                 470                 475                 480
Pro Ser Asp Leu His Pro Thr Met Thr Ala Ala Leu Ile Ser Asn Lys
                485                 490                 495
Pro Glu Phe Val Lys Leu Phe Leu Glu Asn Gly Val Gln Leu Lys Glu
                500                 505                 510
Phe Val Thr Trp Asp Thr Leu Leu Tyr Leu Tyr Glu Asn Leu Asp Pro
                515                 520                 525
Ser Cys Leu Phe His Ser Lys Leu Gln Lys Val Leu Val Glu Asp Pro
    530                 535                 540
Glu Arg Pro Ala Cys Ala Pro Ala Ala Pro Arg Leu Gln Met His His
545                 550                 555                 560
Val Ala Gln Val Leu Arg Glu Leu Leu Gly Asp Phe Thr Gln Pro Leu
                565                 570                 575
Tyr Pro Arg Pro Arg His Asn Asp Arg Leu Arg Leu Leu Leu Pro Val
                580                 585                 590
Pro His Val Lys Leu Asn Val Gln Gly Val Ser Leu Arg Ser Leu Tyr
                595                 600                 605
Lys Arg Ser Ser Gly His Val Thr Phe Thr Met Asp Pro Ile Arg Asp
    610                 615                 620
Leu Leu Ile Trp Ala Ile Val Gln Asn Arg Arg Glu Leu Ala Gly Ile
625                 630                 635                 640
Ile Trp Ala Gln Ser Gln Asp Cys Ile Ala Ala Leu Ala Cys Ser
                645                 650                 655
Lys Ile Leu Lys Glu Leu Ser Lys Glu Glu Asp Thr Asp Ser Ser
                660                 665                 670
Glu Glu Met Leu Ala Leu Ala Glu Glu Tyr Glu His Arg Ala Ile Gly
                675                 680                 685
Val Phe Thr Glu Cys Tyr Arg Lys Asp Glu Glu Arg Ala Gln Lys Leu
                690                 695                 700
Leu Thr Arg Val Ser Glu Ala Trp Gly Lys Thr Thr Cys Leu Gln Leu
705                 710                 715                 720
Ala Leu Glu Ala Lys Asp Met Lys Phe Val Ser His Gly Gly Ile Gln
                725                 730                 735
Ala Phe Leu Thr Lys Val Trp Trp Gly Gln Leu Ser Val Asp Asn Gly
                740                 745                 750
Leu Trp Arg Val Thr Leu Cys Met Leu Ala Phe Pro Leu Leu Leu Thr
                755                 760                 765
Gly Leu Ile Ser Phe Arg Glu Lys Arg Leu Gln Asp Val Gly Thr Pro
                770                 775                 780
```

-continued

```
Ala Ala Arg Ala Arg Ala Phe Phe Thr Ala Pro Val Val Phe His
785                 790                 795                 800

Leu Asn Ile Leu Ser Tyr Phe Ala Phe Leu Cys Leu Phe Ala Tyr Val
                    805                 810                 815

Leu Met Val Asp Phe Gln Pro Val Pro Ser Trp Cys Glu Cys Ala Ile
                820                 825                 830

Tyr Leu Trp Leu Phe Ser Leu Val Cys Glu Glu Met Arg Gln Leu Phe
                835                 840                 845

Tyr Asp Pro Asp Glu Cys Gly Leu Met Lys Lys Ala Ala Leu Tyr Phe
                850                 855                 860

Ser Asp Phe Trp Asn Lys Leu Asp Val Gly Ala Ile Leu Leu Phe Val
865                 870                 875                 880

Ala Gly Leu Thr Cys Arg Leu Ile Pro Ala Thr Leu Tyr Pro Gly Arg
                    885                 890                 895

Val Ile Leu Ser Leu Asp Phe Ile Leu Phe Cys Leu Arg Leu Met His
                900                 905                 910

Ile Phe Thr Ile Ser Lys Thr Leu Gly Pro Lys Ile Ile Ile Val Lys
                915                 920                 925

Arg Met Met Lys Asp Val Phe Phe Leu Phe Leu Leu Ala Val Trp
930                 935                 940

Val Val Ser Phe Gly Val Ala Lys Gln Ala Ile Leu Ile His Asn Glu
945                 950                 955                 960

Arg Arg Val Asp Trp Leu Phe Arg Gly Ala Val Tyr His Ser Tyr Leu
                965                 970                 975

Thr Ile Phe Gly Gln Ile Pro Gly Tyr Ile Asp Gly Val Asn Phe Asn
                980                 985                 990

Pro Glu His Cys Ser Pro Asn Gly Thr Asp Pro Tyr Lys Pro Lys Cys
                995                 1000                1005

Pro Glu Ser Asp Ala Thr Gln Gln Arg Pro Ala Phe Pro Glu Trp Leu
                1010                1015                1020

Thr Val Leu Leu Leu Cys Leu Tyr Leu Leu Phe Thr Asn Ile Leu Leu
1025                1030                1035                1040

Leu Asn Leu Leu Ile Ala Met Phe Asn Tyr Thr Phe Gln Gln Val Gln
                    1045                1050                1055

Glu His Thr Asp Gln Ile Trp Lys Phe Gln Arg His Asp Leu Ile Glu
                1060                1065                1070

Glu Tyr His Gly Arg Pro Ala Ala Pro Pro Pro Phe Ile Leu Leu Ser
                1075                1080                1085

His Leu Gln Leu Phe Ile Lys Arg Val Val Leu Lys Thr Pro Ala Lys
                1090                1095                1100

Arg His Lys Gln Leu Lys Asn Lys Leu Glu Lys Asn Glu Glu Ala Ala
1105                1110                1115                1120

Leu Leu Ser Trp Glu Ile Tyr Leu Lys Glu Asn Tyr Leu Gln Asn Arg
                    1125                1130                1135

Gln Phe Gln Gln Lys Gln Arg Pro Glu Gln Lys Ile Glu Asp Ile Ser
                1140                1145                1150

Asn Lys Val Asp Ala Met Val Asp Leu Leu Asp Leu Asp Pro Leu Lys
                1155                1160                1165

Arg Ser Gly Ser Met Glu Gln Arg Leu Ala Ser Leu Glu Glu Gln Val
                1170                1175                1180

Ala Gln Thr Ala Arg Ala Leu His Trp Ile Val Arg Thr Leu Arg Ala
1185                1190                1195                1200
```

-continued

```
Ser Gly Phe Ser Ser Glu Ala Asp Val Pro Thr Leu Ala Ser Gln Lys
                1205                1210                1215

Ala Ala Glu Glu Pro Asp Ala Glu Pro Gly Gly Arg Lys Lys Thr Glu
            1220                1225                1230

Glu Pro Gly Asp Ser Tyr His Val Asn Ala Arg His Leu Leu Tyr Pro
            1235                1240                1245

Asn Cys Pro Val Thr Arg Phe Pro Val Pro Asn Glu Lys Val Pro Trp
1250                    1255                1260

Glu Thr Glu Phe Leu Ile Tyr Asp Pro Pro Phe Tyr Thr Ala Glu Arg
1265                    1270                1275                1280

Lys Asp Ala Ala Ala Met Asp Pro Met Gly Asp Thr Leu Glu Pro Leu
                1285                1290                1295

Ser Thr Ile Gln Tyr Asn Val Val Asp Gly Leu Arg Asp Arg Arg Ser
                1300                1305                1310

Phe His Gly Pro Tyr Thr Val Gln Ala Gly Leu Pro Leu Asn Pro Met
                1315                1320                1325

Gly Arg Thr Gly Leu Arg Gly Arg Gly Ser Leu Ser Cys Phe Gly Pro
    1330                1335                1340

Asn His Thr Leu Tyr Pro Met Val Thr Arg Trp Arg Arg Asn Glu Asp
1345                    1350                1355                1360

Gly Ala Ile Cys Arg Lys Ser Ile Lys Lys Met Leu Glu Val Leu Val
                1365                1370                1375

Val Lys Leu Pro Leu Ser Glu His Trp Ala Leu Pro Gly Gly Ser Arg
                1380                1385                1390

Glu Pro Gly Glu Met Leu Pro Arg Lys Leu Lys Arg Ile Leu Arg Gln
                1395                1400                1405

Glu His Trp Pro Ser Phe Glu Asn Leu Leu Lys Cys Gly Met Glu Val
    1410                1415                1420

Tyr Lys Gly Tyr Met Asp Asp Pro Arg Asn Thr Asp Asn Ala Trp Ile
1425                    1430                1435                1440

Glu Thr Val Ala Val Ser Val His Phe Gln Asp Gln Asn Asp Val Glu
                1445                1450                1455

Leu Asn Arg Leu Asn Ser Asn Leu His Ala Cys Asp Ser Gly Ala Ser
                1460                1465                1470

Ile Arg Trp Gln Val Val Asp Arg Arg Ile Pro Leu Tyr Ala Asn His
            1475                1480                1485

Lys Thr Leu Leu Gln Lys Ala Ala Ala Glu Phe Gly Ala His Tyr
            1490                1495                1500
```